United States Patent [19]

Gearing

[11] Patent Number: 5,262,522
[45] Date of Patent: Nov. 16, 1993

[54] RECEPTOR FOR ONCOSTATIN M AND LEUKEMIA INHIBITORY FACTOR

[75] Inventor: David P. Gearing, Seattle, Wash.

[73] Assignee: Immunex Corporation, Seattle, Wash.

[21] Appl. No.: 797,556

[22] Filed: Nov. 22, 1991

[51] Int. Cl.$^5$ .................. C07K 13/00; C12N 15/62
[52] U.S. Cl. ................... 530/350; 435/69.7; 435/252.3; 435/370.1
[58] Field of Search .............. 435/69.1, 69.7; 530/350, 387; 536/27

[56] References Cited

U.S. PATENT DOCUMENTS 5,073,627 12/1991 Curtis et al. .................... 530/351
5,155,027 10/1992 Sledziewski et al. .

FOREIGN PATENT DOCUMENTS 0411946 2/1991 European Pat. Off. .

OTHER PUBLICATIONS

Hibi et al., "Molecular Cloning and Expression of an IL-6 Signal Transducer, gp130", *Cell* 63:1149 (Dec. 1990).

Gearing et al., "Leukemia inhibitory of factor receptor is structurally related to the IL-6 signal transducrer, gp130", *The EMBO Journal* 10(10):2839 (Oct. 1991).

Gearing and Cosman, "Homology of the p40 Subunit of Natural Killer Cell Stimulatory Factor (NKSF) with the Extracellular Domain of the Interleukin-6 Receptor", *Cell* 66:9 (Jul. 1991).

Linsley et al., "Identification and Characterization of Cellular Receptors for the Growth Regulator, Oncostatin M", *J. Biol. Chem.* 264(8):4282 (Mar. 1989).

Lesslauer et al., "Recombinant soluble tumor necrosis factor receptor proteins protect mice from lipopolysaccharide-induced lethality", *Eur. J. Immunol* 21:2883 (Nov. 1991).

Peppel and Beutler, "Chimeric TNF-R—IgG Molecule Acts As Soluble Inhibitor of TNF Mediated Cytotoxicity", *J. Cell. Biochem.* (*ABSTR*), *Suppl.* 15F (Apr. 1991).

Brown et al., "Regulation of IL-6 Expression by Oncostatin M", *J. Immunol.* 147:2175 (Oct. 1991).

DeWit et al., "Interleukin-6 concentrations in the serum of patients with AIDS-associated Kaposi's sarcoma during treatment with interferon-alpha", *J. Intern. Med.* 229:539 (Jun. 1991).

Primary Examiner—Robert J. Hill, Jr.
Assistant Examiner—John D. Ulm
Attorney, Agent, or Firm—Kathryn A. Seese

[57] ABSTRACT

A receptor protein comprising a gp130 polypeptide linked to a single-chain leukemia inhibitory factor receptor (LIF-R) polypeptide is capable of binding both oncostatin M and leukemia inhibitory factor (LIF). The receptor protein binds LIF with greater affinity than does the single-chain LIF-R polypeptide alone. The receptor may be produced as a fusion protein in recombinant cells. The gp130 polypeptide binds oncostatin M, but with lower affinity than does the inventive receptor protein.

9 Claims, 8 Drawing Sheets

RECEPTOR FOR ONCOSTATIN M AND LEUKEMIA INHIBITORY FACTOR

BACKGROUND OF THE INVENTION

Receptors that bind specific molecules (e.g., a hormone, drug, cytokine, or biochemical) have been identified on a multitude of cell types. Receptors are found on the cell surface or, in the case of soluble receptors, are released into the serum. Effort has been directed toward isolation and characterization of a number of receptors in order to study their physiological roles and to explore possible therapeutic uses. The binding of a particular target molecule by a soluble receptor administered to a patient may alleviate disorders mediated by the target molecule.

Certain receptors have been found to comprise two separate polypeptide chains associated in the form of a complex. Such two-chain receptors often bind the target molecule with greater affinity than that exhibited by one of the chains alone.

Leukemia inhibitory factor (LIF) is a polypeptide hormone that plays a central role in the regulation of diverse adult and embryonic systems. LIF acts on a variety of cell types and has multiple biological activities. The diversity in biological activity is reflected in the various synonyms of LIF, which include hepatocyte stimulating factor III (Baumann and Wong, *J. Immunol.* 143:1163 [1989]); cholinergic nerve differentiation factor (Yamamori et al., *Science* 246:1412 [1990]); melanoma-derived lipoprotein lipase inhibitor (Mori et al., *Biochem. Biophys. Res. Comm.* 160:1085 [1989]); human interleukin for DA cells (Moreau et al., *Nature* 336:690 [1988]); differentiation factor (Tomida et al., *J. Biol. Chem.* 259:10978 [1984]); differentiation inhibitory factor (Abe et al., *J. Biol. Chem.* 264; 8941 [1989]); differentiation inhibitory activity (Smith and Hooper, *Devel. Biol.*; 121:1 [1987]); and differentiation retarding factor (Koopman and Cotton, *Exp. Cell Res.* 154:233 [1984].

The cloning of a leukemia inhibitory factor receptor (LIF-R) has been reported by Gearing et al. in *EMBO J.* 10:2839 (1991). This recombinant single-chain LIF-R polypeptide binds LIF, but with lower affinity than the naturally occurring LIF receptors found on certain normal cells. A receptor that binds LIF with higher affinity than that exhibited by this cloned single chain LIF-R would be desirable for certain applications.

Oncostatin M is a secreted single-chain polypeptide cytokine that regulates the growth of certain tumor-derived and normal cell lines. Oncostatin M is produced by activated lymphoid cells. A number of cell types have been found to bind the oncostatin M protein. See, for example, Linsley et al., *J. Biol. Chem.*, 264:4282 (1989). However, the isolation and characterization of an oncostatin M receptor have not been reported.

SUMMARY OF THE INVENTION

The present invention provides a receptor that has the property of binding both oncostatin M and leukemia inhibitory factor (LIF). The receptor comprises gp130 linked (preferably covalently) to leukemia inhibitory factor receptor (LIF-R). The gp130 polypeptide may be covalently linked to the LIF-R polypeptide by any suitable means, such as via a cross-linking reagent or a polypeptide linker. In one embodiment of the invention, the receptor is a fusion protein produced by recombinant DNA technology. Disorders mediated by either oncostatin M or LIF may be treated by administering a therapeutically effective amount of the inventive receptor to a patient afflicted with such a disorder.

BRIEF DESCRIPTION OF THE DRAWINGS

FIG. 5 presents composite DNA and encoded amino acid sequences of a full length LIF-R, determined by comparing the sequences of cDNA and genomic clones. The signal peptidase cleavage site is marked with a vertical arrow. The transmembrane region is heavily underlined. Potential N-linked glycosylation sites are marked with asterisks. Hallmark residues associated with the hematopoietin family of receptors are shown boxed. The horizontal arrow marks the point at which genomic sequence was used to derive the 3' coding region of LIF-R, since the cDNA clones employed in determining this sequence terminated with a stretch of A nucleotides at this point.

FIG. 6 presents the DNA and deduced amino acid sequences of cloned gp130 cDNA as reported by Hibi et al. in *Cell* 63:1149 (1990). A predicted signal sequence is underlined. The thick underline indicates a presumed transmembrane region. The sets of asterisks identify possible N-glycosylation sites.

DETAILED DESCRIPTION OF THE INVENTION

Figure 1:
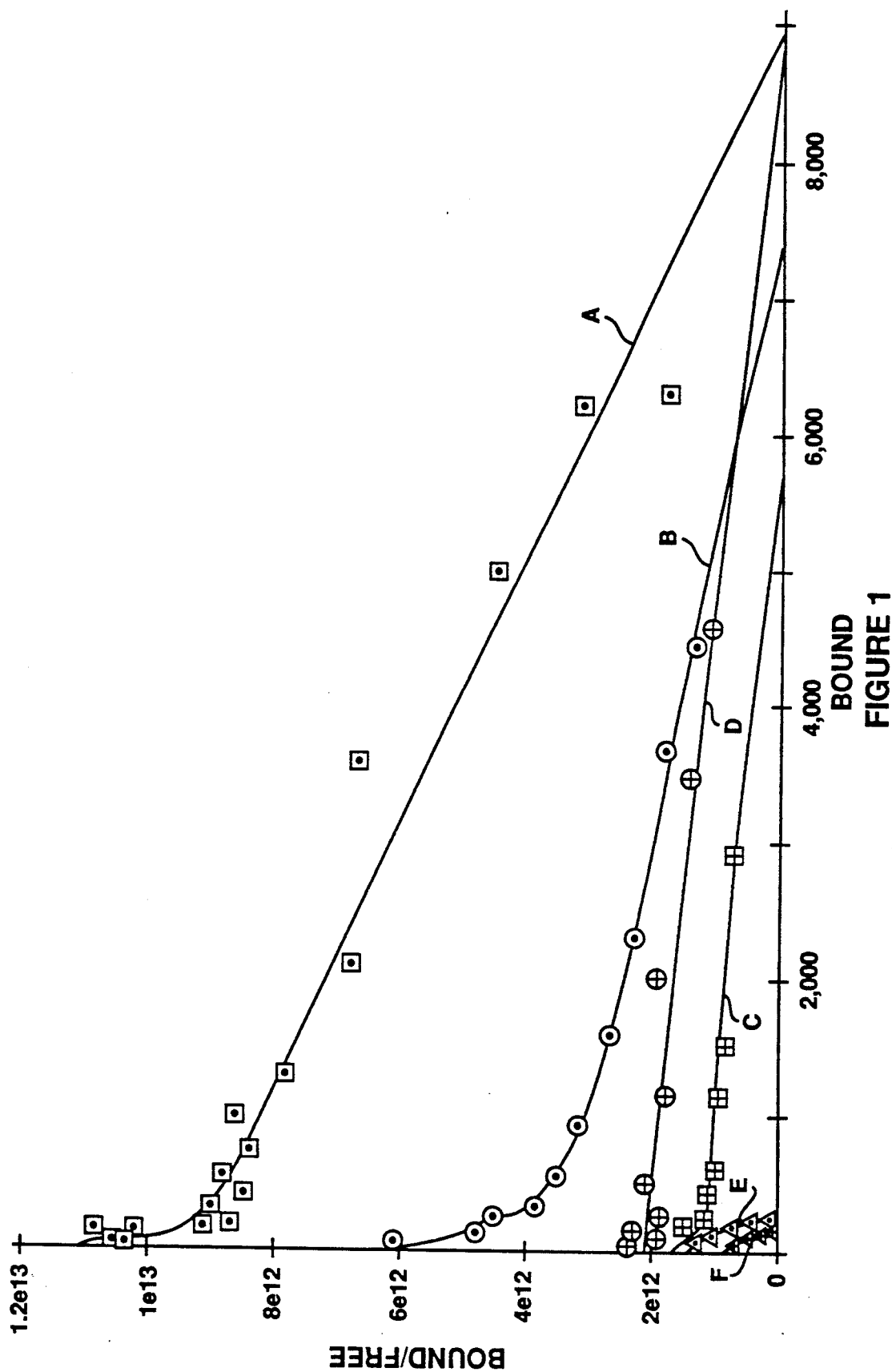
FIG. 1 is a graph presenting the results of an LIF binding assay. Host cells transfected with vector(s) encoding gp130 or LIF-R were assayed for the ability to bind LIF, as described in example 1.

The present invention provides a receptor comprising gp130 covalently linked to leukemia inhibitory factor receptor (LIF-R). In another embodiment of the invention, the receptor comprises gp130 non-covalently complexed with LIF-R. The receptor is capable of binding oncostatin M, and also binds leukemia inhibitory factor (LIF). The receptor thus is useful for treating disorders mediated by either oncostatin M or LIF.

The gp130 may be covalently linked to the LIF-R by any suitable means, such as via a cross-linking reagent or a polypeptide linker. The gp130 and LIF-R proteins are covalently linked in a manner that does not interfere with the resulting receptor's ability to bind oncostatin M and LIF. In one embodiment of the invention, the receptor is a fusion protein produced by recombinant DNA technology.

Non-covalent bonding of gp130 to LIF-R may be achieved by any suitable means that does not interfere with the receptor's ability to bind oncostatin M and LIF. In one approach, a first compound is attached to LIF-R and a second compound that will non-covalently bond to the first compound is attached to gp130. Examples of such compounds are biotin and avidin. The receptor is thus formed through the non-covalent interactions of biotin with avidin. In one embodiment of the invention, LIF-R and gp130 are recombinant polypeptides, each purified from recombinant cells and then non-covalently bonded together to form the receptor. A host cell may be transformed with two different expression vectors such that both LIF-R and gp130 are produced by the recombinant host cell. LIF-R and gp130 (one or both of which are soluble fragments as described below) produced by such transformed host cells may associate to form a complex through non-covalent interactions.

"Leukemia inhibitory factor receptor" (LIF-R) refers to a protein (a cytokine receptor) that is present on the surface of various hematopoietic cells, including monocytemacrophages and megakaryocytes, and on non-hematopoietic cells, including osteoblasts, placental trophoblasts, and liver parenchymal cells. LIF-R is capable of binding leukemia inhibitory factor (LIF) molecules and plays a role in transducing the signal provided by LIF to a cell. In the absence of any species designation, LIF-R refers generically to mammalian LIF-R, which includes, but is not limited to, human, murine, and bovine LIF-R.

Figure 5:
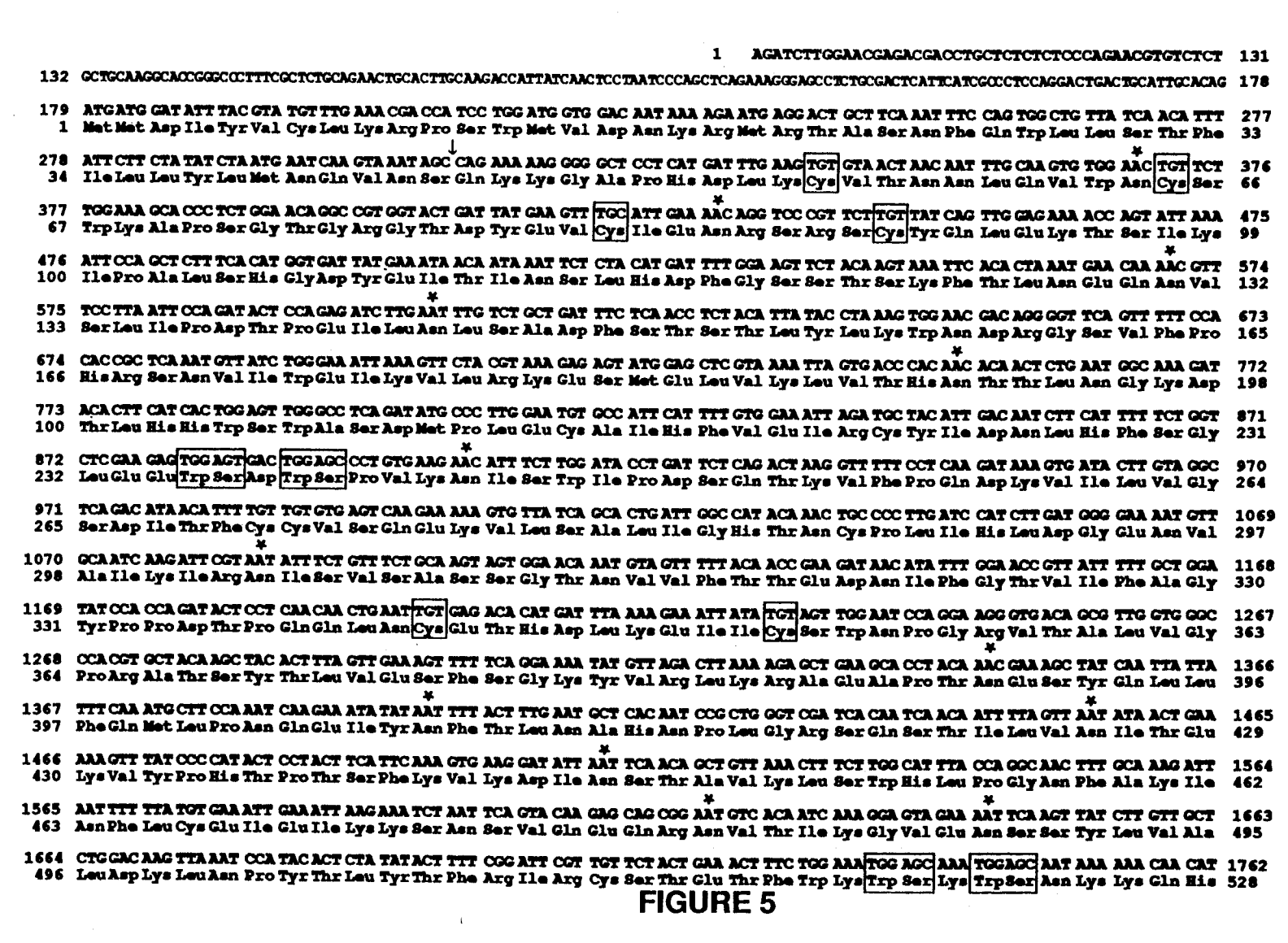
Figure 5:
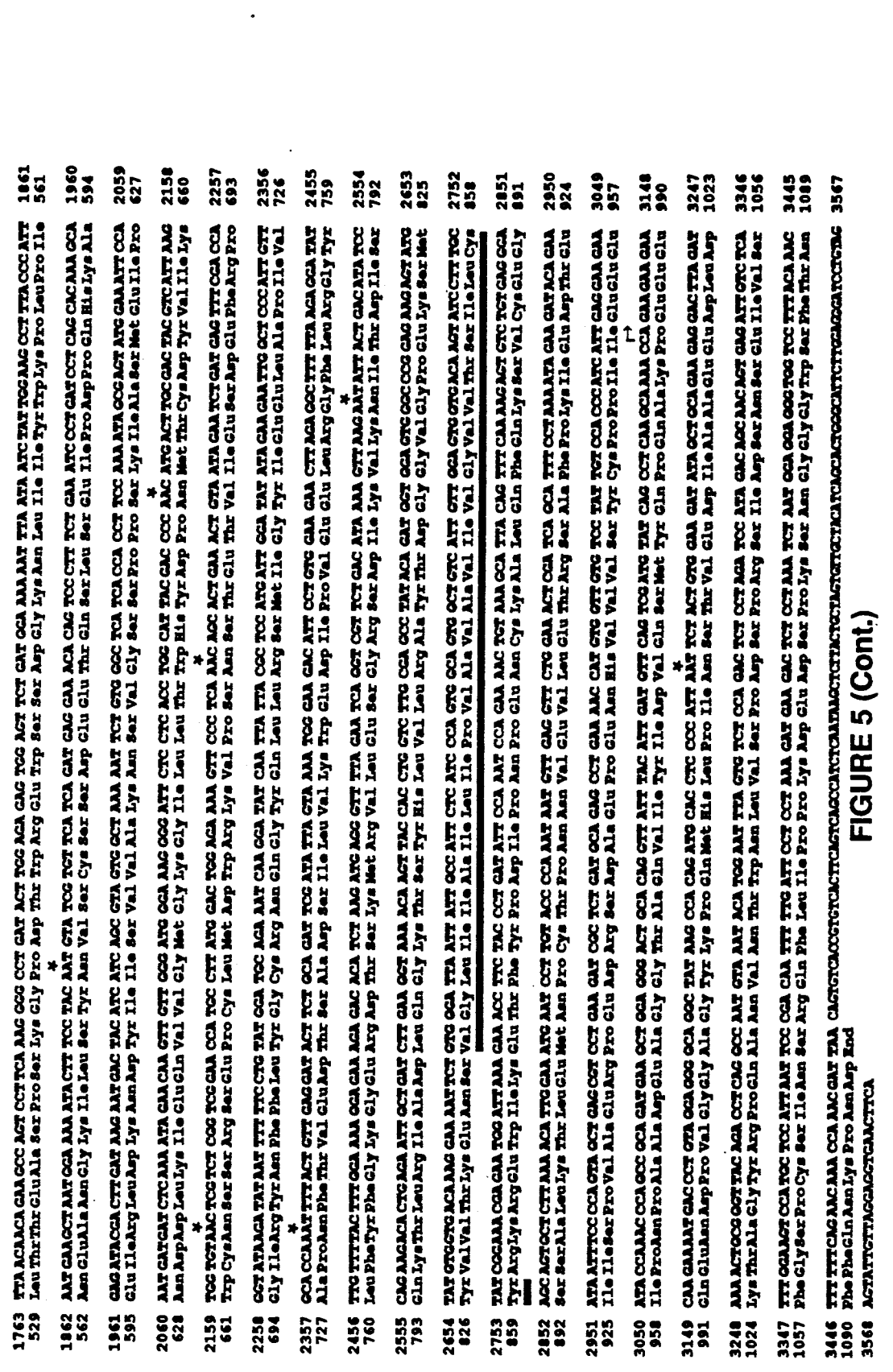

The cloning of human and murine leukemia inhibitory factor receptors (LIF-R), each a single polypeptide chain, has been reported by Gearing et al. in *EMBO J.* 10:2839 (1991), which is hereby incorporated by reference in its entirety. The DNA sequence of a human LIF-R cDNA clone and the amino acid sequence encoded thereby are shown in SEQ ID NO: 5 and SEQ ID NO: 6. This cloned human cDNA encodes an N-terminal fragment of human LIF-R that includes (in order from N-terminus to C-terminus) a 44-amino acid signal sequence (amino acids −44 to −1), the entire extracellular region, a transmembrane region (the first amino acid of which is amino acid number 790 of SEQ ID NO: 5) and a portion of the cytoplasmic domain. The C-terminus of the fragment includes amino acids encoded by a poly-A segment and by a linker employed in vector construction, as described in Gearing et al., supra. The term "transmembrane region" as used herein refers to a string of hydrophobic amino acids positioned between the extracellular domain and the cytoplasmic domain of the protein. A plasmid vector containing the above-described cloned human LIF-R cDNA is designated pHLIFR-65 and has been deposited in *E. coli* host cells with the American Type Culture Collection on Dec. 11, 1990 (ATCC accession no. 68491). The DNA and amino acid sequences of a full length native human LIF-R (determined by comparing the sequences of cDNA and genomic clones) have been reported by Gearing et al. supra and are presented herein in FIG. 5.

The LIF-R encoded by the cloned cDNA (SEQ ID NO: 6) contains the entire extracellular region of LIF-R (the domain believed to be responsible for the LIF-binding activity), and binds LIF, but with lower affinity than does a naturally occurring LIF receptor found on certain normal cells. Additionally, oncostatin M competes with LIF for binding to naturally occurring high affinity LIF receptors on certain cell types (Gearing et al., *New Biologist*, in press) but did not bind to the above-described cloned LIF-R expressed in COS cells.

In order to investigate the possible existance of a high affinity converting subunit for the cloned single polypeptide chain LIF-R, host cells were co-transfected with the LIF-R encoding plasmid pHLIFR-65 and with pools from a human placental cDNA library (also contained in an expression vector). The co-transfected cells were assayed for the ability to bind radiolabeled oncostatin M.

A positive cDNA pool was subdivided and the procedure repeated to isolate a single cDNA clone designated B10G that conferred the ability to bind oncostatin M on cells co-transfected with B10G and the LIF-R encoding plasmid pHLIFR-65. The co-transfected cells also were found to bind LIF with higher affinity than cells transfected with pHLIFR-65 alone. Host cells transfected with B10G alone exhibited low affinity oncostatin M binding sites. The B10G cloned cDNA was sequenced and found to encode a protein that is known as gp130.

Thus, it has now been found that a receptor comprising both LIF-R and gp130 binds LIF with higher affinity than does the single-chain LIF-R polypeptide alone. The improved LIF binding of LIF-R in combination with gp130 is described in example 1 below and depicted in FIG. 1.

Although LIF does not bind to either high- or low-affinity oncostatin M receptors, it has now been found that oncostatin M binds to the receptors of the present invention comprising LIF-R and gp130. Oncostatin M binding is described in example 2 below and depicted in FIG. 2.

Figure 6:
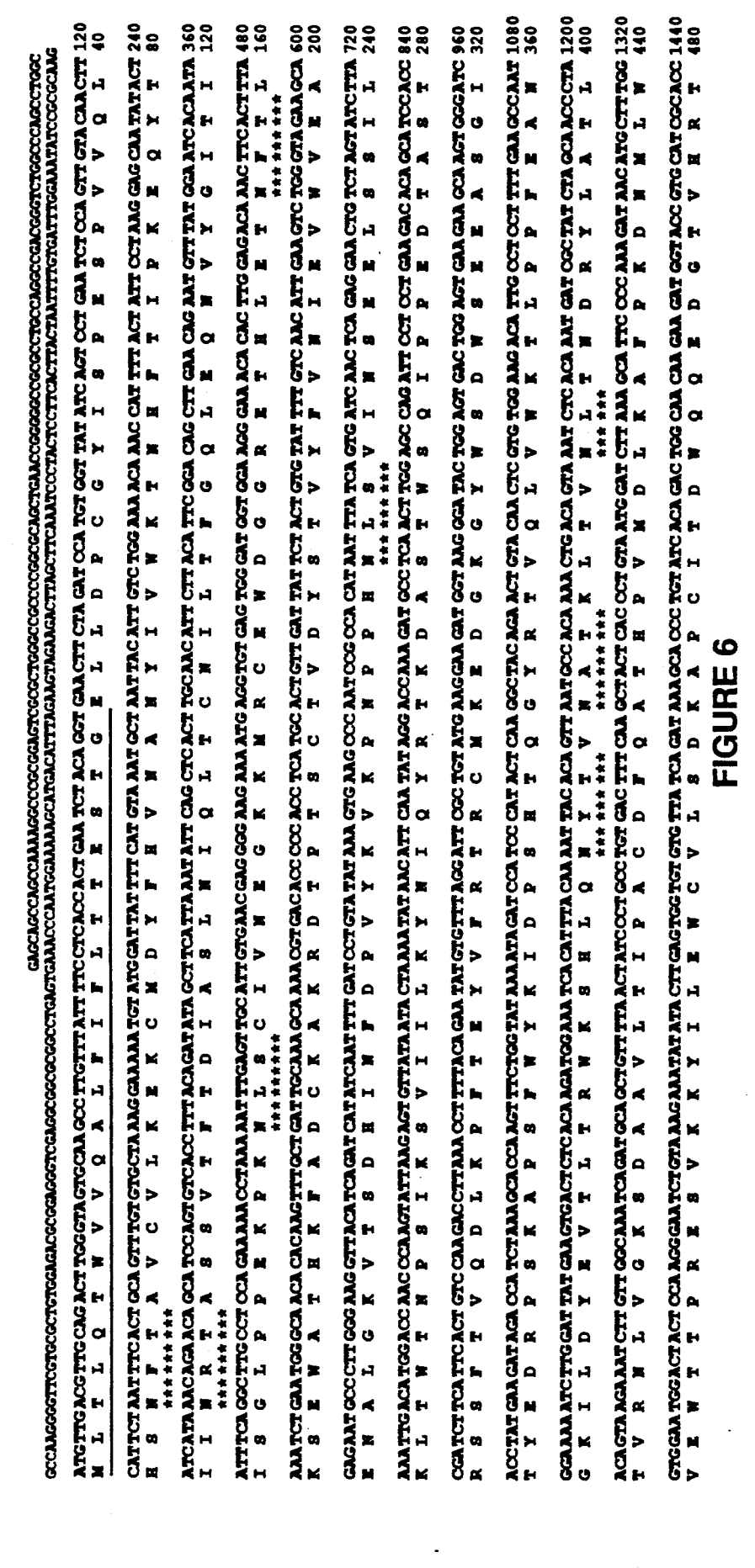
Figure 6:
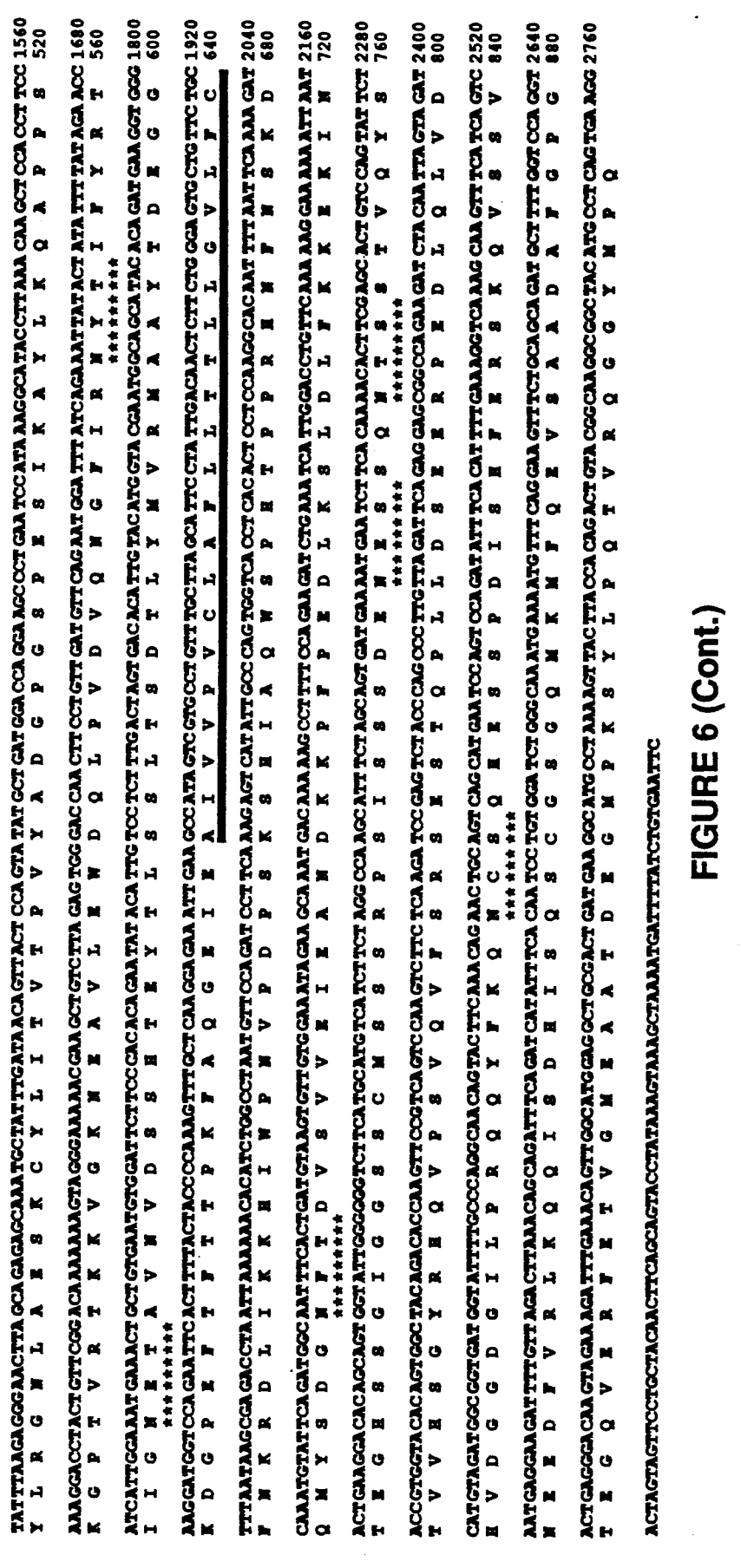

A protein known as gp130 has been purified from cellular sources that include placental tissue and a myeloma cell line U266. A number of additional cell types have been found to express gp130 mRNA, as reported by Hibi et al., in *Cell* 63:1149 (1990). gp130 has been reported to be involved in the formation of high affinity interleukin-6 binding sites and in IL-6 signal transduction (Hibi et al. supra). The cloning and expression of cDNA encoding a full length gp130 protein has been reported by Hibi et al., supra, which is hereby incorporated by reference in its entirety. The DNA and deduced amino acid sequences reported by Hibi et al. for the gp130 cloned cDNA are presented herein in FIG. 6. The gp130 amino acid sequence may vary from that reported by Hibi et al., e.g., leucine may be substituted for valine at position 8 in the signal sequence (numbering is as shown in FIG. 6). This amino acid substitution may be attributable to genetic polymorphism (allelic variation among individuals producing the protein), and results from the presence of C rather than G at nucleotide position 22.

As used herein, the term LIF-R includes variants and truncated forms of native LIF-R proteins that possess the desired LIF-binding or signal transducing activity. Likewise, the term gp130 as used herein includes variants and truncated forms of the native gp130 protein that retain the desired biological activity. For gp130, the desired biological activity includes binding of oncostatin M; conferring on the inventive receptor the ability to bind oncostatin M; and increasing the affinity of the inventive receptor for LIF, compared to the LIF binding affinity of the single-chain LIF-R polypeptide alone. Specifically included are truncated, soluble or fusion forms of LIF-R and gp130, as described below. Variants produced by adding, substituting, or deleting amino acid(s) in the native sequence are discussed in more detail below.

One example of an LIF-R polypeptide that may be employed is that encoded by the cDNA clone designated pHLIF-R-65 (SEQ ID NO: 5), as described by Gearing et al., supra and in example 3 below. Alternatively, a fragment comprising amino acids 1 to 945 of SEQ ID NO: 5 may be employed. Amino acid 945 is the last LIF-R-specific amino acid of the polypeptide encoded by clone pHLIF-R-65, before the poly-A nucleotide segment believed to result from oligo(dT) priming at an internal site in the mRNA during preparation of the hLIF-R cDNA. (See Gearing et al., supra. at page 2840, column one.)

Other examples of LIF-R polypeptides that may be employed in the inventive receptors include those lacking all or part of the transmembrane region or the cytoplasmic domain of the protein. Suitable LIF-R polypeptides thus include those containing amino acids 1-x or, when the signal sequence is not desired, amino acids 45-x of the full length LIF-R sequence depicted in FIG. 5, wherein x represents an integer from 833 to 1096. Amino acid number 833 is the last amino acid of the extracellular domain (i.e., before the start of the transmembrane region.) Polypeptides terminating in amino acid number 1096 lack the last C-terminal amino acid of the full length protein. The desirability of including the signal sequence depends on such factors as the position of LIF-R in a fusion protein, as discussed below, and the intended host cells when the receptor is to be produced via recombinant DNA technology. Note that the numbering of amino acids in FIG. 5 (taken from Gearing et al., supra) differs from that of SEQ ID NO: 5 because the first amino acid of the signal sequence is designated amino acid number 1 in FIG. 5 but is designated −44 in SEQ ID NO: 5. Other polypeptides may be chosen with regard to sequences that are conserved in the hematopoietin receptor family, (i.e., chosen to include the boxed sequence(s) shown in FIG. 5.)

One example of a suitable gp130 polypeptide is that encoded by cDNA cloned into plasmid vector pDC303 to produce a plasmid designated B10G. The source of mRNA used in producing the cDNA was human placental tissue. Plasmid B10G in E. coli strain DH5α host cells was deposited with the American Type Culture Collection, Rockville, Md., on Nov. 14, 1991, and assigned ATCC accession number 68827.

The DNA sequence of the gp130 cDNA contained in plasmid B10G and the amino acid sequence of the gp130 protein encoded by the cloned cDNA are presented in SEQ ID NO: 1 and SEQ ID NO: 2. The protein comprises (in order from the N-terminus to the C-terminus) a 22-amino acid signal sequence, complete extracellular domain (amino acids 1–597), a transmembrane region (beginning with amino acid 598), and a partial cytoplasmic domain (amino acids 621–686). This truncated gp130 polypeptide differs from the equivalent portion of the Hibi et al. protein in that the eighth amino acid of the signal sequence is leucine rather than valine, discussed above.

Another example of a suitable gp130 polypeptide comprises amino acids 1 to 496 of the SEQ ID NO: 1, which includes all of the cysteine residues found in the extracellular domain of the protein, and also contains a complete fibronectin domain. Additional examples of gp130 polypeptides are those comprising amino acids 1–298 or 98–298 of SEQ ID NO: 1.

Other gp130 polypeptides lacking all or part of the transmembrane region and/or cytoplasmic domain may be employed. Suitable gp130 polypeptides thus include those containing amino acids 1−x or, when the signal sequence is not desired, amino acids 23−x of the FIG. 6 sequence, wherein x represents an integer from 619 to 917. The first amino acid of the transmembrane region is the alanine residue at position 620 in FIG. 6. Polypeptides terminating at amino acid 917 lack the last C-terminal amino acid of the full length protein presented in FIG. 6. Note that the numbering of amino acids in FIG. 6 (taken from Hibi et al., supra) differs from that shown in SEQ ID NO: 1 and NO: 2 because the first amino acid of the signal sequence is designated amino acid number 1 in FIG. 6 but is designated −22 in SEQ ID NO: 1. Regions of the gp130 protein corresponding to domains that are conserved among certain receptors are discussed by Hibi et al, supra, at page 1150, column 2, and page 1151, column 1. Other truncated gp130 polypeptides chosen to include these conserved regions may be employed.

Preferred LIF-R and gp130 polypeptides are those which are soluble. In one embodiment of the present invention, the receptor comprises soluble LIF-R covalently attached to soluble gp130. "Soluble LIF-R" as used in the context of the present invention refers to polypeptides that are substantially similar in amino acid sequence to all or part of the extracellular region of a native LIF-R and that, due to the lack of a transmembrane region that would cause retention of the polypeptide on a cell membrane, are secreted upon expression. The soluble LIF-R polypeptides that may be employed retain the ability to bind LIF or, by competitively binding LIF, inhibit LIF signal transduction activity via cell surface bound LIF-R proteins. Soluble LIF-R may also include part of the transmembrane region or part of the cytoplasmic domain or other sequences, provided that the soluble LIF-R protein is capable of being secreted. Likewise, the term "soluble gp130" as used herein refers to proteins that are substantially similar in amino acid sequence to all or part of the extracellular region of a native gp130 and are secreted upon expression but retain the desired biological activity. Soluble gp130 may include part of the transmembrane region, cytoplasmic domain, or other sequences, as long as the polypeptide is secreted.

Soluble LIF-R and soluble gp130 may be identified (and distinguished from their non-soluble membrane-bound counterparts) by separating intact cells which express the desired protein from the culture medium, e.g., by centrifugation, and assaying the medium (supernatant) for the presence of the desired protein. The culture medium may be assayed using procedures which are similar or identical to those described in the examples below. The presence of LIF-R or gp130 in the medium indicates that the protein was secreted from the cells and thus is a soluble form of the desired protein. Soluble LIF-R and soluble gp130 may be naturally-occurring forms of these proteins. Cloning of a naturally-occurring soluble murine LIF-R is reported in Gearing et al., supra. Alternatively, soluble fragments of LIF-R and gp130 proteins may be produced by recombinant DNA technology or otherwise isolated, as described below.

The use of soluble forms of LIF-R and gp130 is advantageous for certain applications. Purification of the proteins from recombinant host cells is facilitated, since the soluble proteins are secreted from the cells. Further, soluble proteins are generally more suitable for intravenous administration and may exert their therapeutic effect (binding LIF and oncostatin M) in the bloodstream.

Preferred soluble LIF-R polypeptides include the signal sequence and entire extracellular domain (amino acids −44 to 789 of SEQ ID NO: 5) or lack the signal sequence but contain the entire extracellular domain (amino acids 1 to 789 of SEQ ID NO: 5). Preferred soluble gp130 polypeptides include the signal sequence and entire extracellular domain (amino acids −22 to 597 of SEQ ID NO: 1) or lack the signal sequence but contain the entire extracellular domain (amino acids 1 to 597 of SEQ ID NO: 1). The preparation and use of these preferred soluble polypeptides in receptors of the present invention is described in examples 3-5.

Truncated LIF-R and gp130, including soluble polypeptides, may be prepared by any of a number of conventional techniques. In the case of recombinant proteins, a DNA fragment encoding a desired fragment may be subcloned into an expression vector. Alternatively, a desired DNA sequence may be chemically synthesized using known techniques. DNA fragments also may be produced by restriction endonuclease digestion of a full length cloned DNA sequence, and isolated by electrophoresis on agarose gels. Linkers containing restriction endonuclease cleavage site(s) may be employed to insert the desired DNA fragment into an expression vector, or the fragment may be digested at cleavage sites naturally present therein. Alternatively, proteins may be fragmented using proteolytic enzymes, for example, and the desired truncated polypeptide isolated from the digestion mixture using reversed phase HPLC.

The well known polymerase chain reaction procedure also may be employed to isolate a DNA sequence encoding a desired protein fragment. This technique is illustrated in examples 3-5 below.

In another approach, enzymatic treatment (e.g., using Bal 31 exonuclease) may be employed to delete terminal nucleotides from a DNA fragment to obtain a fragment having a particular desired terminus. Among the commercially available linkers are those that can be ligated to the blunt ends produced by Bal 31 digestion, and which contain restriction endonuclease cleavage site(s). Alternatively, oligonucleotides that reconstruct the N- or C-terminus of a DNA fragment to a desired point may be synthesized. The oligonucleotide may contain a restriction endonuclease cleavage site upstream of the desired coding sequence and position an initiation codon (ATG) at the N-terminus of the coding sequence.

The gp130 polypeptide is attached to the LIF-R polypeptide through a covalent or non-covalent linkage. Covalent attachment is preferred for certain applications, e.g. in vivo use, in view of the enhanced stability generally conferred by covalent, as opposed to non-covalent, bonds. In constructing the receptor of the present invention, covalent linkage may be accomplished via cross-linking reagents, polypeptide linkers, or any other suitable technique.

Numerous reagents useful for cross-linking one protein molecule to another are known. Heterobifunctional and homobifunctional linkers are available for this purpose from Pierce Chemical Company, Rockford, Ill., for example. Such linkers contain two functional groups (e.g., esters and/or maleimides) that will react with certain functional groups on amino acid side chains, thus linking one polypeptide to another. The reagent and reaction conditions should be chosen such that the cross-linking does not interfere with binding of oncostatin M and LIF to the receptor.

One type of polypeptide linker that may be employed in the present invention separates gp130 and LIF-R domains by a distance sufficient to ensure that each domain properly folds into the secondary and tertiary structures necessary for the desired biological activity. The linker also should allow the extracellular domains of gp130 and LIF-R to assume the proper spatial orientation to form the binding site for oncostatin M and LIF. Suitable polypeptide linkers preferably (1) will adopt a flexible extended conformation, (2) will not exhibit a propensity for developing an ordered secondary structure which could interact with the functional gp130 and LIF-R domains, and (3) will have minimal hydrophobic or charged character which could promote interaction with the functional protein domains. Typical surface amino acids in flexible protein regions include Gly, Asn and Ser. Virtually any permutation of amino acid sequences containing Gly, Asn and Ser would be expected to satisfy the above criteria for a peptide linker sequence. Other near neutral amino acids, such as Thr and Ala, may also be used in the linker sequence. Examples of such polypeptide linkers are presented below.

Figure 4:
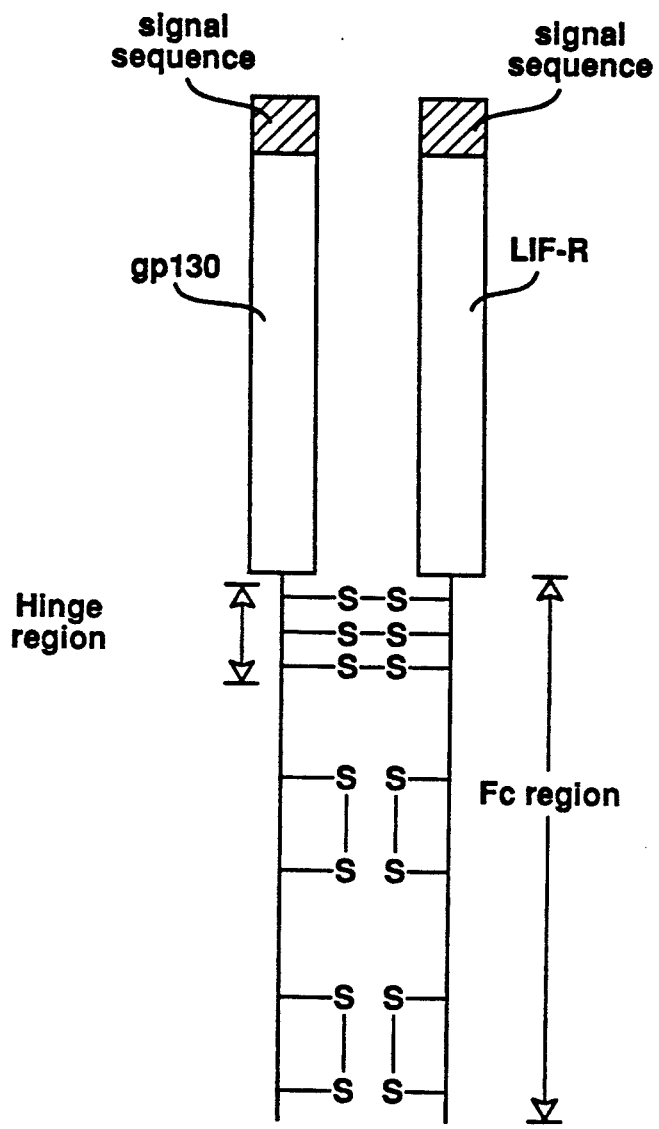
FIG. 4 schematically depicts a receptor of the present invention wherein Fc polypeptides derived from an antibody are used to link a gp130 fragment to an LIF-R fragment.

Another type of polypeptide linker that may be employed comprises the Fc region of an antibody. An Fc polypeptide is attached to the C-terminus of LIF-R or of the LIF-R fragment. A separate Fc polypeptide is attached to the C-terminus of gp130 or of the gp130 fragment. The two resulting polypeptide chains may be combined in a buffered solution, whereupon disulfide bonds form between the two Fc polypeptides (e.g., in the so-called hinge region, where interchain disulfide bonds are normally present in antibody molecules). Alternatively, a host cell may be transformed with DNA encoding both polypeptides such that the two polypeptides are co-expressed and interchain disulfide bonds form in the host cell. LIF-R is thus covalently linked to gp130 via the disulfide bonds in the linker portion of the receptor. Procedures for isolating the Fc region of an antibody are well-known and include proteolytic digestion with papain. Alternatively, an Fc polypeptide may be produced by recombinant cells or chemically synthesized. Also useful are N-terminal fragments of an antibody Fc region that contain the cysteine residues involved in disulfide bond formation at the hinge region. One example of a receptor containing an Fc polypeptide linker is illustrated in example 5 below. The receptor is depicted in FIG. 4. The number and position of disulfide bonds may vary from those shown in FIG. 4.

In an alternative embodiment, a first fusion polypeptide comprising gp130 (or fragment thereof) upstream of an antibody light chain (or a fragment thereof) is prepared. A second second fusion polypeptide comprises LIF-R upstream of an antibody heavy chain (or a heavy chain fragment, the N-terminus of which extends at least through the $C_H1$ region. Disulfide bond(s) form between the gp130-light chain fusion polypeptide and the LIF-R-heavy chain fusion polypeptide, thus producing a receptor of the present invention comprising a polypeptide linker. If desired, a third fusion (an LIF-R-antibody light chain fusion polypeptide) is prepared and combined with (disulfide bonded to) a fourth fusion comprising gp130 fused to an antibody heavy chain. When the two disulfide bonded molecules are combined, additional disulfide bonds form between the two Fc regions. The resulting receptor of the present invention comprising the four fusion polypeptides resembles an antibody in structure and displays the oncostatin M/LIF binding site bivalently.

A polypeptide linker may be attached to gp130 and to LIF-R by any of the conventional procedures used to attach one polypeptide to another. The cross-linking reagents available from Pierce Chemical Company as described above are among those that may be employed. Amino acids having side chains reactive with such reagents may be included in the polypeptide linker, e.g., at the termini thereof.

The gp130 and LIF-R polypeptides may be separately purified from cellular sources, and then linked together. Alternatively, the receptor of the present invention may be produced using recombinant DNA technology. The gp130 and LIF-R polypeptides may be produced separately and purified from transformed host cells for subsequent covalent linkage. In one embodiment of the present invention, a host cell is transformed/transfected with foreign DNA that encodes gp130 and LIF-R as separate polypeptides. The two polypeptides may be encoded by the same expression vector with start and stop codons for each of the two genes, or the recombinant cells may be co-transfected with two separate expression vectors. In another embodiment, the receptor is produced as a fusion protein in recombinant cells.

In one embodiment of the present invention, the receptor protein is a recombinant fusion protein of the formula:

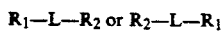

$$R_1-L-R_2 \text{ or } R_2-L-R_1$$

wherein $R_1$ represents gp130 or a gp130 fragment; $R_2$ represents LIF-R or an LIF-R fragment; and L represents a polypeptide linker.

The fusion proteins of the present invention include constructs in which the C-terminal portion of gp130 is fused to the linker which is fused to the N-terminal portion of LIF-R, and also constructs in which the C-terminal portion of LIF-R is fused to the linker which is fused to the N-terminal portion of gp130. gp130 is covalently linked to LIF-R in such a manner as to produce a single protein which retains the desired biological activities of gp130 and LIF-R. The components of the fusion protein are listed in their order of occurrence (i.e., the N-terminal polypeptide is listed first, followed by the linker and then the C-terminal polypeptide).

A DNA sequence encoding a fusion protein is constructed using recombinant DNA techniques to insert separate DNA fragments encoding gp130 and LIF-R into an appropriate expression vector. The 3' end of a DNA fragment encoding gp130 is ligated (via the linker) to the 5' end of the DNA fragment encoding LIF-R with the reading frames of the sequences in phase to permit translation of the mRNA into a single biologically active fusion protein. Alternatively, the 5' end of a DNA fragment encoding LIF-R may be ligated (via the linker) to the 5' end of the DNA fragment encoding gp130, with the reading frames of the sequences in phase to permit translation of the mRNA into a single biologically active fusion protein. A DNA sequence encoding an N-terminal signal sequence may be retained on the DNA sequence encoding the N-terminal polypeptide, while stop codons, which would prevent read-through to the second (C-terminal) DNA sequence, are eliminated. Conversely, a stop codon required to end translation is retained on the second DNA sequence. DNA encoding a signal sequence is preferably removed from the DNA sequence encoding the C-terminal polypeptide.

Suitable polypeptide linkers comprise a chain of amino acids, preferably from 20 to 100 amino acids in length and most preferably from 30 to 60 amino acids in length. As discussed above, the linker advantageously comprises amino acids selected from the group consisting of glycine, asparagine, serine, threonine, and alanine. Examples of suitable polypeptide linkers include, but are not limited to, $(Gly_4Ser)_n$, wherein n is 4–12, preferably 8, and $(Gly_4SerGly_5Ser)_2$.

A DNA sequence encoding a desired polypeptide linker may be inserted between, and in the same reading frame as, the DNA sequences encoding gp130 and LIF-R using any suitable conventional technique. For example, a chemically synthesized oligonucleotide encoding the linker and containing appropriate restriction endonuclease cleavage sites may be ligated between the sequences encoding gp130 and LIF-R.

Alternatively, a chemically synthesized DNA sequence may contain a sequence complementary to the 3' terminus (without the stop codon) of either gp130 or LIF-R, followed by a linker-encoding sequence which is followed by a sequence complementary to the 5' terminus of the other of gp130 and LIF-R. Oligonucleotide directed mutagenesis is then employed to insert the linker-encoding sequence into a vector containing a direct fusion of gp130 and LIF-R.

The present invention provides an isolated DNA sequence encoding the above-described fusion protein comprising gp130, LIF-R, and a polypeptide linker, and also provides recombinant expression vectors containing the isolated DNA sequence. "Expression vector" refers to a replicable DNA construct used to express DNA which encodes the desired protein and which includes a transcriptional unit comprising an assembly of (1) genetic element(s) having a regulatory role in gene expression, for example, promoters, operators, or enhancers, operatively linked to (2) a DNA sequence encoding a desired protein (in this case, a receptor of the present invention) which is transcribed into mRNA and translated into protein, and (3) appropriate transcription and translation initiation and termination sequences. The choice of promoter and other regulatory elements generally varies according to the intended host cell.

Proteins to be produced in yeast expression systems preferably include a leader sequence enabling extracellular secretion of translated protein by the yeast host cell. Alternatively, where recombinant protein is expressed without a leader or transport sequence, it may include an N-terminal methionine residue. This residue optionally may be subsequently cleaved from the expressed recombinant protein to provide a final product.

In the expression vectors, regulatory elements controlling transcription or translation are generally derived from mammalian, microbial, viral or insect genes. The ability to replicate in a host, usually conferred by an origin of replication, and a selection gene to facilitate recognition of transformants may additionally be incorporated. Vectors derived from retroviruses also may be employed.

DNA regions are operably linked when they are functionally related to each other. For example, DNA encoding a signal peptide (secretory leader) is operably linked to DNA for a polypeptide if the polypeptide is expressed as a precursor that is secreted through the host cell membrane; a promoter is operably linked to a coding sequence if it controls the transcription of the sequence; or a ribosome binding site is operably linked to a coding sequence if it is positioned so as to permit translation. Generally, "operably linked" means contiguous and, in the case of secretory leaders, contiguous and in reading frame.

Transformed host cells are cells which have been transformed or transfected with foreign DNA using recombinant DNA techniques. In the context of the present invention, the foreign DNA includes a sequence encoding the inventive receptor. Host cells may be transformed for purposes of cloning of amplifying the foreign DNA, or may be transformed with an expression vector for production of the receptor protein. Suitable host cells for expression of the receptor include prokaryotes, yeast or higher eukaryotic cells under the control of appropriate promoters. Prokaryotes include gram negative or gram positive organisms, for example *E. coli* or bacilli. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Examples of suitable prokaryotic hosts for transformation include *E. coli, Bacillus subtilis, Salmonella typhimurium*, and various species within the genera Pseudomonas, Streptomyces, and Staphylococcus, although others may also be employed as a matter of choice. Higher eukaryotic cells include established cell lines of mammalian origin. Cell-free translation systems could also be employed to produce fusion protein using RNAs derived from the DNA constructs of the present invention. Appropriate cloning and expression vectors for use with bacterial, fungal, yeast, and mammalian cellular hosts are described by Pouwels et al. (*Cloning Vectors: A Laboratory Manual*, Elsevier, N.Y., 1985), the relevant disclosure of which is hereby incorporated by reference.

Useful expression vectors for bacterial use can comprise a selectable marker and bacterial origin of replication derived from commercially available plasmids comprising genetic elements of the well-known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and this provides simple means for identifying transformed cells.

Promoters commonly used in recombinant microbial expression vectors include the b-lactamase (penicillinase) and lactose promoter system (Chang et al., *Nature* 275:615, 1978; and Goeddel et al., *Nature* 281:544, 1979), the tryptophan (trp) promoter system (Goeddel et al., *Nucl. Acids Res.* 8:4057, 1980; and EPA 36,776) and tac promoter (Maniatis, *Molecular Cloning: A Laboratory Manual*, Cold Spring Harbor Laboratory, p. 412, 1982). A particularly useful bacterial expression system employs the phage λ $P_L$ promoter and cI857ts thermoinducible repressor. Plasmid vectors available from the American Type Culture Collection which incorporate derivatives of the λ $P_L$ promoter include plasmid pHUB2, resident in *E. coli* strain JMB9 (ATCC 37092) and pPLc28, resident in *E. coli* RR1 (ATCC 53082).

The recombinant receptor protein may also be expressed in yeast hosts, preferably from Saccharomyces species, such as *S. cerevisiae*. Yeast of other genera such as Pichia or Kluyveromyces may also be employed. Yeast vectors will generally contain an origin of replication from the 2 μm yeast plasmid or an autonomously replicating sequence (ARS), a promoter, DNA encoding the receptor fusion protein, sequences for polyadenylation and transcription termination and a selection gene. Preferably, yeast vectors will include an origin of replication and selectable markers permitting transformation of both yeast and *E. coli*, e.g., the ampicillin resistance gene of *E. coli* and the *S. cerevisiae* trp1 gene, which provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase. Suitable vectors and promoters for use in yeast expression are further described in R. Hitzeman et al., EPA 73,657.

Preferred yeast vectors can be assembled using DNA sequences from pBR322 for selection and replication in *E. coli* (Amp$^r$ gene and origin of replication) and yeast DNA sequences including a glucose-repressible ADH2 promoter and α-factor secretion leader. The ADH2 promoter has been described by Russell et al. (*J. Biol. Chem.* 258:2674, 1982) and Beier et al., (*Nature* 300:724, 1982). The yeast α-factor leader, which directs secretion of heterologous proteins, can be inserted between the promoter and the structural gene to be expressed. See, e.g., Kurjan et al., *Cell* 30:922, 1982; and Bitter et al., *Proc. Natl. Acad. Sci. USA* 81:5330, 1984. The leader sequence may be modified to contain, near its 3' end, one or more useful restriction sites to facilitate fusion of the leader sequence to foreign genes.

Suitable yeast transformation protocols are known to those of skill in the art. An exemplary technique is described by Hinnen et al., *Proc. Natl. Acad. Sci. USA* 75:1929, (1978), selecting for Trp+ transformants in a selective medium consisting of 0.67% yeast nitrogen base, 0.5% casamino acids, 2% glucose, 10 μg/ml uracil.

Host strains transformed by vectors comprising the ADH2 promoter may be grown for expression in a rich medium consisting of 1% yeast extract, 2% peptone, and 1% glucose supplemented with 80 μg/ml adenine and 80 μg/ml uracil. Derepression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow and Summers, *Bio/Technology* 6:47 (1988). Examples of suitable mammalian host cell lines include the COS-7 lines of monkey kidney cells, described by Gluzman (*Cell* 23:175, 1981), and other cell lines capable of expressing an appropriate vector including, for examples, L cells, C127, 3T3, Chinese hamster ovary (CHO), HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin or replication (Fiers et al., *Nature* 273:113, 1978). Smaller or larger SV40 fragments may also be used, provided the approximately 250 bp sequence extending from the Hind III site toward the Bg/I site located in the viral origin of replication is included. Exemplary vectors can be constructed as disclosed by Okayama and Berg (*Mol. Cell. Biol.* 3:280, 1983).

A useful system for stable high level expression of mammalian receptor cDNAs in C127 murine mammary epithelial cells can be constructed substantially as described by Cosman et al. (*Mol. Immunol.* 23:935, 1986).

Particularly preferred vectors for expression of the inventive receptor as a fusion protein are described in the examples below. The foregoing discussion is, of course, applicable to the production of recombinant fusion proteins comprising a fragment of gp130 and/or a fragment of LIF-R. Suitable fragments are discussed above, and DNA sequences encoding such fragments may be inserted into the above-described expression vectors.

The present invention provides a process for preparing the recombinant receptor of the present invention, comprising culturing a host cell transformed with an expression vector comprising a DNA sequence that encodes said receptor under conditions that promote expression. The receptor is then purified from culture media or cell extracts.

For example, supernatants from systems which secrete recombinant protein into the culture medium can be first concentrated using a commercially available protein concentration filter, for example, an Amicon or Millipore Pellicon ultrafiltration unit. Following the concentration step, the concentrate can be applied to a suitable purification matrix. For example, a suitable affinity matrix can comprise LIF or OSM. An LIF affinity matrix may be prepared by coupling recombinant human LIF to cyanogen bromide-activated Sepharose (Pharmacia) or Hydrazide Affigel (Biorad), according to manufacturer's recommendations. Sequential immunopurification using antibodies bound to a suitable support is preferred. Proteins binding to an antibody specific for LIF-R are recovered and contacted with antibody specific for gp130 on an insoluble support. Proteins immunoreactive with both antibodies may thus be identified and isolated. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. One or more reversed-phase high performance liquid chromatography (RP-HPLC) steps employing hydrophobic RP-HPLC media, e.g., silica gel having pendant methyl or other aliphatic groups, can be employed to further purify a fusion protein composition.

Some or all of the foregoing purification steps, in various combinations, can be employed to provide an essentially homogeneous recombinant protein. Recombinant cell culture enables the production of the fusion protein free of those contaminating proteins which may be normally associated with gp130 or LIF-R as they are found in nature in their respective species of origin, e.g., in cells, cell exudates or body fluids.

The foregoing purification procedures are among those that may be employed to purify non-recombinant receptors of the present invention as well. When linking procedures that may produce homodimers (gp130-linker-gp130 and LIF-R-linker-LIF-R) are employed, purification procedures that separate the desired heterodimer from such homodimers are employed. An example of such a procedure is sequential immunopurification as discussed above.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant fusion proteins can disrupted by any convenient method, including freeze-thaw cycling, sonication, mechanical disruption, or use of cell lysing agents.

Fermentation of yeast which express fusion proteins as a secreted protein greatly simplifies purification. Secreted recombinant protein resulting from a large-scale fermentation can be purified by methods analogous to those disclosed by Urdal et al. (*J. Chromatog.* 296:171, 1984), involving two sequential, reversed-phase HPLC steps for purification of a recombinant protein on a preparative HPLC column.

The present invention also provides a pharmaceutical composition comprising a receptor protein of the present invention with a physiologically acceptable carrier or diluent. Such carriers and diluents will be nontoxic to recipients at the dosages and concentrations employed. Such compositions may, for example, comprise the receptor protein in a buffered solution, to which may be added antioxidants such as ascorbic acid, low molecular weight (less than about ten residues) polypeptides, proteins, amino acids, carbohydrates including glucose, sucrose or dextrins, chelating agents such as EDTA, glutathione and other stabilizers and excipients. The receptor of the present invention may be administered by any suitable method in a manner appropriate to the indication, such as intravaneous injection, continuous infusion, sustained release from implants, etc.

The DNA and/or amino acid sequences of gp130 and LIF-R may vary from those presented in SEQ ID NO: 1 and SEQ ID NO: 5. Due to the known degeneracy of the genetic code, there can be considerable variation in nucleotide sequences encoding the same amino acid sequence. The DNA sequences presented in SEQ ID NO: 1 and SEQ ID NO: 5 are understood to be the coding strand. DNA sequences capable of hybridizing to the so-called (−) strand (the (−) strand being complementary to the DNA sequence of SEQ ID NO: 1 or SEQ ID NO: 5) under moderately stringent conditions (50° C., 2 X SSC), and which encode a biologically active gp130 or LIF-R polypeptide, are also considered to be gp130-encoding or LIF-R-encoding DNA sequences, respectively, in the context of the present invention. Further, certain mutations in a nucleotide sequence which encodes LIF-R or gp130 will not be expressed in the final protein product. For example, nucleotide substitutions may be made to enhance expression, primarily to avoid secondary structure loops in the transcribed mRNA (see EPA 75,444A, incorporated herein by reference). Other alterations of the nucleotide sequence may be made to provide codons that are more readily translated by the selected host, e.g., the well-known E. coli preference codons for E. coli expression.

The amino acid sequence of native gp130 or LIF-R may be varied by substituting, deleting, adding, or inserting one or more amino acids to produce a gp130 or LIF-R variant. Variants that possess the desired biological activity of the native gp130 and LIF-R proteins may be employed in the receptor of the present invention. Assays by which the biological activity of variant proteins may be analyzed are described in the examples below.

Alterations to the native amino acid sequence may be accomplished by any of a number of known techniques. For example, mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craig (*BioTechniques*, January 1985, 12–19); Smith et al. (*Genetic Engineering: Principles and Methods*, Plenum Press, 1981); U.S. Pat. No. 4,518,584, and U.S. Pat. No. 4,737,462, which are incorporated by reference herein.

Bioequivalent variants of LIF-R and gp130 may be constructed by, for example, making various substitutions of amino acid residues or deleting terminal or internal amino acids not needed for biological activity. In one embodiment of the invention, the variant amino acid sequence is at least 80% identical, preferably at least 90% identical, to the native sequence. Percent similarity may be determined, for example, by comparing sequence information using the GAP computer program, version 6.0, available from the University of Wisconsin Genetics Computer Group (UWGCG). The GAP program utilizes the alignment method of Needleman and Wunsch (J. Mol. Biol. 48:443, 1970), as revised by Smith and Waterman (Adv. Appl. Math. 2:482, 1981). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

Generally, substitutions should be made conservatively; i.e., the most preferred substitute amino acids are those having physiochemical characteristics resembling those of the residue to be replaced. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Moreover, particular amino acid differences between human, murine and other mammalian LIF-Rs is suggestive of additional conservative substitutions that may be made without altering the essential biological characteristics of LIF-R.

Cysteine residues can be deleted or replaced with other amino acids to prevent formation of unnecessary or incorrect intramolecular disulfide bridges upon renaturation. Other approaches to mutagenesis involve modification of adjacent dibasic amino acid residues to enhance expression in yeast systems in which KEX2 protease activity is present. Hydrophilic amino acids may be substituted for hydrophobic amino acids in the transmembrane region and/or intracellular domain of gp130 and LIF-R to enhance water solubility of the proteins. Addition of amino acids to the native sequence may result from translation of in-frame codons present in linkers used in constructing cloning or expression vectors. The LIF-R encoded by clone pHLIF-R-65 contains such linker-encoded amino acids at the C-terminus, as described by Gearing et al., supra.

The present invention also includes proteins with or without associated native-pattern glycosylation. Expression of DNAs encoding the fusion proteins in bacteria such as *E. coli* provides non-glycosylated molecules. Functional mutant analogs having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where A1 is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between $A_1$ and Z, or an amino acid other than Asn between Asn and $A_1$.

Variants of the receptor proteins of the present invention also include various structural forms of the primary protein which retain biological activity. Due to the presence of ionizable amino and carboxyl groups, for example, a receptor protein may be in the form of acidic or basic salts, or may be in neutral form. Individual amino acid residues may also be modified by oxidation or reduction.

The primary amino acid structure also may be modified by forming covalent or aggregative conjugates with other chemical moieties, such as glycosyl groups, lipids, phosphate, acetyl groups and the like. Covalent derivatives are prepared by linking particular functional groups to amino acid side chains or at the N- or C-termini. Other derivatives of the receptor protein within the scope of this invention include covalent or aggregative conjugates of the receptor protein with other proteins or polypeptides, such as by synthesis in recombinant culture as N- or C-terminal fusions. For example, the conjugated polypeptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast a-factor leader). Peptides may also be added to facilitate purification or identification of the fusion protein (e.g., poly-His). The amino acid sequence of the fusion protein can also be linked to the peptide Asp-Tyr-Lys-Asp-Asp-Asp-Asp-Lys (DYKDDDDK) (Hopp et al., *Bio/Technology* 6:1204, 1988). The latter sequence is highly antigenic and provides an epitope reversibly bound by a specific monoclonal antibody, enabling rapid assay and facile purification of expressed recombinant protein. This sequence is also specifically cleaved by bovine mucosal enterokinase at the residue immediately following the Asp-Lys pairing. Receptor proteins capped with this peptide may also be resistant to intracellular degradation in *E. coli*.

The receptors of the present invention are primarily useful as oncostatin M binding reagents, and may be administered in vivo to inhibit a biological activity of oncostatin M (including signal transduction). The inventive receptors also have use as LIF binding reagents.

Disorders mediated by either oncostatin M or LIF may be treated by administering a therapeutically effective amount of the receptor of the present invention to a human or mammalian patient afflicted with such a disorder. A disorder is said to be mediated by oncostatin M or LIF when biologically active oncostatin M or LIF causes (directly or indirectly) or exacerbates the disorder. Soluble receptor proteins can be used to competitively bind to LIF and oncostatin M, thereby inhibiting binding of LIF and oncostatin M to cell surface receptors.

As discussed in example 2, gp130 has now been found to bind oncostatin M, although with lower affinity than the inventive receptors comprising both gp130 and LIF-R. gp130 may be administered to treat conditions mediated by oncostatin M, although a gp130/LIF-R receptor of the present invention would be preferred for such a purpose.

Oncostatin M has been reported to stimulate hematopoiesis, stimulate epithelial cell proliferation, increase plasmin activity (thereby inducing fibrinolysis), inhibit angiogenesis and supress expression of major histocompatibility complex antigens on endothelial cells. See PCT application WO 9109057 and European patent application no. 422,186. When these or other biological effects of oncostatin M are undesirable, a receptor of the present invention may be administered to bind oncostatin M.

Oncostatin M is believed to stimulate production of the cytokine interleukin-6 (IL-6), as reported by Brown et al., *J. Immunol.* 147:2175 (1991). Oncostatin M therefore indirectly mediates disorders associated with the presence of IL-6. IL-6 has been reported to be involved in the pathogenesis of AIDS-associated Kaposi's sarcoma (deWit et al., *J. Intern. Med.* [*England*] 229:539 [1991]). Binding of oncostatin M by a receptor of the present invention thus may be useful in treating Kaposi's sarcoma. Alternatively, but less preferably, gp130 may be administered to treat Kaposi's sarcoma.

Among the disorders mediated by LIF are lipoprotein metabolism defects such as atherosclerosis and obesity, as well as disorders of bone and calcium metabolism or disorders associated with LIF overproduction that affect hepatocytes, neurons, or leukocytes. The regulation of embryonic and hematopoietic stem cells by LIF may also be manipulated with the receptor. A soluble form of the receptor may also be used to treat leukemic cells which respond to LIF by proliferating. LIF also may play a role in inducing cachexia in cancer or AIDS patients. The receptor, or antibodies thereto, may also be useful as a diagnositic reagent to detect diseases characterized by the presence of abnormal LIF-R.

Oncostatin M and LIF are different proteins, but share certain structural and biological properties. If inhibition of a biological activity shared by oncostatin M and LIF is desired, the receptor of the present invention offers the benefit of binding both of these proteins exhibiting the particular biological activity. A receptor binding only one of the proteins would leave the other protein active and continuing to mediate the disorder.

Receptor proteins or derivatives thereof may also be used as reagents in receptor-based immunoassays, reagents in assays for oncostatin M or LIF, or as binding agents for affinity purification of oncostatin M or LIF. The receptor proteins of the present invention may be used as immunogens in conventional procedures for production of polyclonal or monoclonal antibodies. Such antibodies may be employed on immunoaffinity columns for purification of the receptor, or as components of diagnostic or research assays. Derivatives may also be obtained by attacking additional polypeptide(s), e.g., by using a cross-linking agent, such as N-maleimidobenzoyl succinimide ester that reacts with cysteine and lysine residues. Receptor proteins may also be covalently bound through reactive side groups to various insoluble substrates, such as cyanogen bromide-activated, bisoxirane-activated, carbonyldiimidazole-activated or tosyl-activated agarose structures, or by adsorbing to polyolefin surfaces (with or without glutaraldehyde cross-linking).

The following examples are provided to illustrate certain embodiments of the invention, and are not to be construed as limiting the scope of the invention.

EXAMPLES

EXAMPLE 1

Assay to Detect Binding of LIF

Recombinant human LIF is expressed in yeast and purified to homogeneity essentially as described by Hopp, et al., *Bio/Technology* 6:1204 (1988). The purified protein is radiolabeled using a commercially available enzymobead radioiodination reagent (BioRad). In this procedure 10 μg LIF in 50 μl 0.2M sodium phosphate, pH 7.2, are combined with 50 μl enzymobead reagent, 2 mCi of sodium iodide in 20 μl of 0.05M sodium phosphate pH 7.0 and 10 μl of 2.5% β-D-glucose. After 10 minutes at 25° C., sodium azide (20 μl of 50 mM) and sodium metabisulfite (10 μl of 5 mg/ml) are added and incubation is continued for 5 min. at 25° C. The reaction mixture is fractionated by gel filtration on a 2 ml bed volume of Sephadex® G-25 (Sigma) equilibrated in Roswell Park Memorial Institute (RPMI) 1640 medium containing 2.5% (w/v) bovine serum albumin (BSA), 0.2% (w/v) sodium azide and 20 mM Hepes pH 7.4 (binding medium). The final pool of $^{125}$I-LIF is diluted to a working stock solution of $3 \times 10^{-8}$M in binding medium and stored for up to one month at 4° C. without detectable loss of receptor binding activity. The specific activity is routinely in the range of $6-8 \times 10^{15}$ cpm/mmole LIF.

The radiolabeled LIF may be employed in any of a number of conventional assay procedures to determine whether a given protein or cell binds LIF. Examples of such assays are those that detect binding of the radiolabeled LIF to cells expressing an LIF-binding protein on the cell surface. The radiolabeled LIF also may be employed in assays for the presence of LIF-binding proteins in cell culture medium (e.g. LIF-binding proteins secreted by recombinant cells). Proteins in cell extracts (e.g. from recombinant cells) also may be assayed for the ability to bind the radiolabeled LIF.

In one assay procedure, cells transformed/transfected with an expression system encoding a protein to be tested for ability to bind LIF are plated at a density of $2 \times 10^5$ cells/well in either 6 well dishes (Falcon) or single well chambered slides (Lab-Tek). Both dishes and slides are pretreated with 1 ml human fibronectin (10 ug/ml in PBS) for 30 minutes followed by 1 wash with PBS. After 48 to 72 hours, cells are assayed for expression of LIF binding proteins by binding radioiodinated LIF using the following slide autoradiography technique. Transfected cells are washed once with binding medium (RPMI media 1640 containing 25 mg/ml bovine serum albumin (BSA), 2 mg/ml sodium azide, 20 mM HEPES, pH 7.2, and 50 mg/ml nonfat dry milk (NFDM) and incubated for 2 hours at 4° C. with 1 ml binding medium+NFDM containing $1.25 \times 10^{-9}$M $^{125}$I-LIF. After incubation, cells in the chambered slides are washed three times with binding buffer+NFDM, followed by 2 washes with PBS, pH 7.3, to remove unbound $^{125}$I-LIF. The cells are fixed by incubating for 30 minutes at room temperature in 10% gluteraldehyde in PBS, pH 7.3, washed twice in PBS, and air dried. The slides are dipped in Kodak NTB-2 photographic emulsion (5× dilution in water) and exposed in the dark for 12 hours to 7 days at 4° C. in a light proof box. The slides are then developed for approximately 5 minutes in Kodak D19 developer (40 g/500 ml water), rinsed in water and fixed in Agfa G433C fixer. The slides are individually examined with a microscope at 25–40× magnification and positive cells that bind LIF are identified by the presence of autoradiographic silver grains against a light background.

Cells in the 6 well plates are washed once with binding buffer+NFDM followed by 3 washings with PBS, pH 7.3, to remove unbound $^{125}$I-LIF. The cells are then trypsinized to remove them from the plate and bound $^{125}$I-LIF is counted on a gamma counter.

The cells in transfectant pool(s) testing positive are subdivided into smaller pools and the screening process is repeated (with further subdividing of the pools as necessary) until an individual clone expressing LIF-binding protein is isolated. Non-specific binding of $^{125}$I-LIF may be measured in the presence of 200-fold or greater excess of unlabeled LIF. As a control, the same host cells transfected with a vector lacking LIF-R-encoding sequences should be assayed to determine whether background endogenous LIF receptors are present on the host cells.

In another assay procedure, cells producing a soluble LIF-binding protein that is released from the cells into the culture medium may be identified. Cells are collected by centrifugation from a culture broth. The supernatant (culture medium) is concentrated 10-fold, and 1 μl aliquots are spotted onto nitrocellulose filters and allowed to air dry. Additional binding sites are blocked by overnight incubation at 4° C. in the above-described binding medium containing 3% non-fat dry milk (BMNFDM). Filters are incubated for 2 h at 4° C. in BMNFDM containing 1 nM $^{125}$I-LIF in the presence or absence of 200 nM unlabeled LIF, then washed (3×5 min) in PBS. Filters are exposed to photographic film for 48 hr at room temperature.

The results of one LIF binding assay conducted according to the following procedure are shown in FIG. 1. Host cells transfected with vector(s) encoding LIF-R or gp130 as described below were assayed for the ability to bind LIF. The host cells were the monkey kidney cell line designated COS-7, described by Glutzman, *Cell* 23:175 (1981). In separate transfections, COS-7 cells were transfected with the following combinations of vectors. The different types of transfected cells (and non-transfected control cells) are designated A–F as shown below, and the curves representing the LIF-binding assay data for each transfected or control cell type are also labeled A–F in FIG. 1.

(A) B10G (the gp130 encoding vector described in example 3) and pHLIFR-65 (the LIF-R encoding vector described in example 3)
(B) pHLIFR-65 and control vector CAV (a control vector that does not encode LIF-R or gp130; controls for plasmid dilution so that results can be more accurately compared with those of COS-7 cells co-transfected with both a gp130 encoding vector and an LIF-R encoding vector)
(C) B10G and pHLIFR-65; transfected cells were preincubated with nonradiolabeled oncostatin M before incubation with $^{125}$I-LIF
(D) pHLIFR-65 and CAV; transfected cells were preincubated with nonradiolabeled oncostatin M before incubation with $^{125}$I-LIF
(E) non-transfected COS-7 cells (control)
(F) B10G and CAV The assay was performed by a phthalate oil separation method essentially as described by Dower et al., *J. Immunol.* 132:751 (1984) and Park et al., *J. Biol. Chem.* 261:4177 (1986). Briefly, the COS-7 host cells were released from 10 cm tissue culture plates two days after transfection by incubation in non-enzymatic cell dissociation buffer (Sigma) at 37° C. for 30–60 minutes. Cells were then washed with the above-described binding medium and resuspended in binding medium at $5 \times 10^6$ cells/ml. 50 μl aliquots of the cells were incubated with serial dilutions of $^{125}$I-LIF at room temperature for one hour with agitation (in the presence or absence of a 200-fold excess of unlabeled LIF) in a total volume of 150 μl. The unlabeled LIF allowed for calculation of the non-specific background binding of LIF. Duplicate aliquots (60 μl) of each incubation mixture were then transferred to a polyethylene centrifuge tube containing a phthalate oil mixture comprising 1.5 parts dibutylphthalate to 1 part bis(s-ethylhexyl)phthalate.

The cells were separated from unbound $^{125}$I-LIF by centrifugation for five minutes at 15,000×g in an Eppendorf microfuge. The centrifuge tubes were cut to separate the pellet of cells (containing bound $^{125}$I-LIF) from the supernatant containing unbound $^{125}$I-LIF. The radioactivity in both parts was then determined on a gamma counter. The determinations of both cell-bound and unbound radioactivity from the two 60 µl aliquots were averaged for subsequent calculations.

The results are presented in FIG. 1 as standard Scatchard transformations of the biological data. The data are reported as the ratio of molecules of $^{125}$I-LIF bound per cell, to free $^{125}$I-LIF molecules (y-axis) versus molecules of $^{125}$I-LIF bound per cell (x-axis). The dissociation constants ($K_D$) are shown in FIG. 1, along with the number of LIF-binding sites per cell. Since a saturating amount of radiolabeled LIF was offered, the number of molecules of radiolabeled LIF bound per cell is considered equivalent to the number of LIF binding sites per cell.

As shown by curve A of FIG. 1, COS-7 cells co-transfected with a gp130 encoding vector (B10G) and an LIF-R encoding vector (pHLIFR-65) demonstrated high affinity LIF binding ($K_D = 9 \times 10^{-10}$M). When these same co-transfected COS-7 cells were preincubated with non-radiolabeled oncostatin M before incubation with $^{125}$I-LIF (curve C), binding of LIF was greatly reduced ($K_D = 4.2 \times 10^{-9}$M). Oncostatin M thus competes with LIF for binding sites on these transfected cells.

COS-7 cells transfected with a vector encoding the single-polypeptide chain LIF-R (pHLIFR-65) and with the control vector CAV bound LIF (curve B; $K_D = 2.4 \times 10^{-9}$M), but with lower affinity than the cells producing both gp130 and LIF-R. The COS-7 cells display endogenous high affinity simian LIF receptors (curve E: $K_D$ about $3 \times 10^{-11}$M). Transfection with pHLIFR-65 (encoding the single polypeptide LIF-R) results in display of additional low affinity LIF receptors ($K_D = 2.4 \times 10^{-9}$M; curve B, site 2) as well as the simian LIF receptors $K_D = 3.3 \times 10^{-11}$M; curve B, site 1).

When the COS-7 cells transfected with pHLIFR-65 and CAV were preincubated with non-radiolabeled oncostatin M before incubation with $^{125}$I-LIF (CURVED), binding of LIF to the LIF-R expressed by pHLIFR-65 was essentially unchanged compared to the same transfected cells not preincubated with oncostatin M. Oncostatin M thus does not compete with LIF for binding to the single polypeptide chain LIF-R. However, the binding of LIF to the endogenous simian high affinity LIF-R on the COS-7 cells was competed.

The COS-7 cells co-transfected with the gp130 encoding vector and the CAV control vector (curve F) did not bind LIF in any measurable amount above the amount of binding to the non-transfected COS-7 cells (curve E).

EXAMPLE 2

Assay to Detect Binding of Oncostatin M

Oncostatin M may be purified from cells in which the protein is naturally found, or from cells transformed with an expression vector encoding oncostatin M. One source of oncostatin M is phorbol ester-treated U937 cells, as described by Zarling et al., *PNAS U.S.A.* 83:9739 (1986). Purification of recombinant oncostatin M is described by Linsley et al., *J. Biol. Chem.* 264:4282-4289 (1989), which is hereby incorporated by reference in its entirety.

Preferably, oncostatin M is produced in yeast cells transformed with a suitable expression vector. A DNA sequence encoding a signal sequence (e.g., a yeast alpha-factor leader sequence) may be fused to the N-terminus of the oncostatin M encoding DNA sequence to promote secretion of the protein from the host cells. The protein when initially produced may also comprise an N-terminal identification leader (e.g., a "flag" sequence such as Asp-Tyr-lys-Asp$_4$-Lys) as described by Hopp et al., *Bio/Technology* 6:1204 (1988). The flag sequence is highly antigenic and provides an epitope reversibly bound by a specific monoclonal antibody, enabling facile purification of the expressed recombinant protein. This sequence is also specifically cleaved by bovine mucosal enterokinase at the residue immediately following the Asp-Lys pairing. Neither the signal sequence nor the flag sequence is found on the processed final oncostatin M product.

Oncostatin M may be radiolabeled using any suitable conventional procedure, such as the radioiodination procedure employed to radiolabel LIF in Example 1. The radio-iodination of oncostatin M has also been described by Linsley et al., supra.

The resulting radiolabeled oncostatin M may be substituted for radiolabeled LIF (using the same concentrations and other reaction parameters) in the assay procedures described in Example 1 in order to detect proteins and cells that bind oncostatin M. An assay for binding of $^{125}$I-oncostatin M to cells is also described in Linsley et al., supra.

Figure 2:
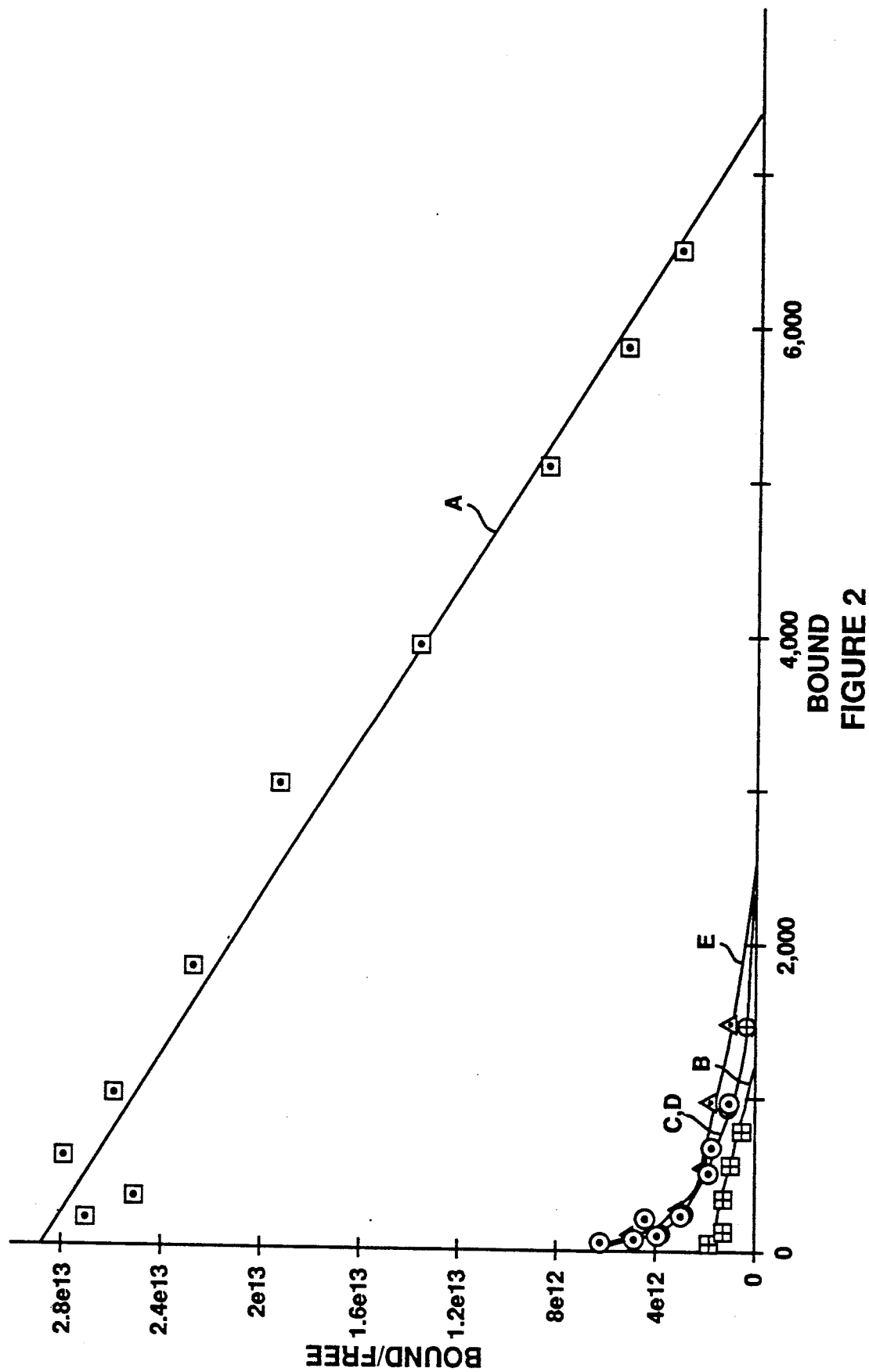
FIG. 2 is a graph presenting the results of an oncostatin M binding assay. Host cells transfected with vector(s) encoding gp130 or LIF-R were assayed for the ability to bind oncostatin M, as described in example 2.

The results of one oncostatin M binding assay are shown in FIG. 2. COS-7 cells transfected with vector(s) encoding gp130 or LIF-R were assayed for the ability to bind oncostatin M. In separate transfections, COS-7 cells were transfected with the following combinations of vectors. The different types of transfected cells (and non-transfected control cells) are designated A-E as shown below, and the corresponding curves representing the oncostatin M binding assay data for each cell type are also labeled A-E in FIG. 2.

(A) B10G (the gp130 encoding vector described in example 3) and pHLIFR-65 (the LIF-R encoding vector described in example 3)

(B) B10G and pHLIFR-65; transfected cells were preincubated with non-radiolabeled LIF before incubation with $^{125}$I-oncostatin M (C) pHLIFR-65 and CAV (a control vector that does not encode LIF-R or gp130; controls for plasmid dilution so that results can be more accurately compared with those of COS-7 cells co-transfected with both a gp130 encoding vector and an LIF-R encoding vector)

(D) non-transfected COS-7 cells (control)

(E) B10G and CAV

The assay was performed by the phthalate oil separation method described in example 1 (but substituting oncostatin M for LIF). The results are presented in FIG. 2 as standard Scatchard transformations of the biological data. The data are reported as the ratio of molecules of $^{125}$I-oncostatin M bound per cell, to free $^{125}$I-oncostatin M molecules (y-axis) versus molecules of $^{125}$I-oncostatin M bound per cell (x-axis). The dissociation constants ($K_D$) are shown in FIG. 2, along with the number of oncostatin M-binding sites per cell. Since a saturating amount of radiolabeled oncostatin M was offered, the number of molecules of radiolabeled oncostatin M bound per cell is considered equivalent to the number of oncostatin M binding sites per cell.

As shown by curve A in FIG. 2, COS-7 cells co-transfected with a gp130 encoding vector (B10G) and an LIF-R encoding vector (pHLIFR-65) demonstrated the ability to bind oncostatin M with high affinity ($K_D$-2.4×10$^{-10}$M).

COS-7 cells co-transfected with a vector encoding the single-polypeptide chain LIF-R (pHLIFR-65) and with the control vector CAV (curve C) did not bind oncostatin M in any significant amount above that bound by the non-transfected COS-7 cells (curve D).

COS-7 cells co-transfected with pHLIFR-65 and B10G and preincubated with non-radiolabeled LIF before incubation with $^{125}$I-oncostatin M (curve B) did not bind oncostatin M in any measurable amount above that bound by the non-transfected COS-7 cells. LIF thus competes with oncostatin M for binding sites on the recombinant cells.

Figure 3:
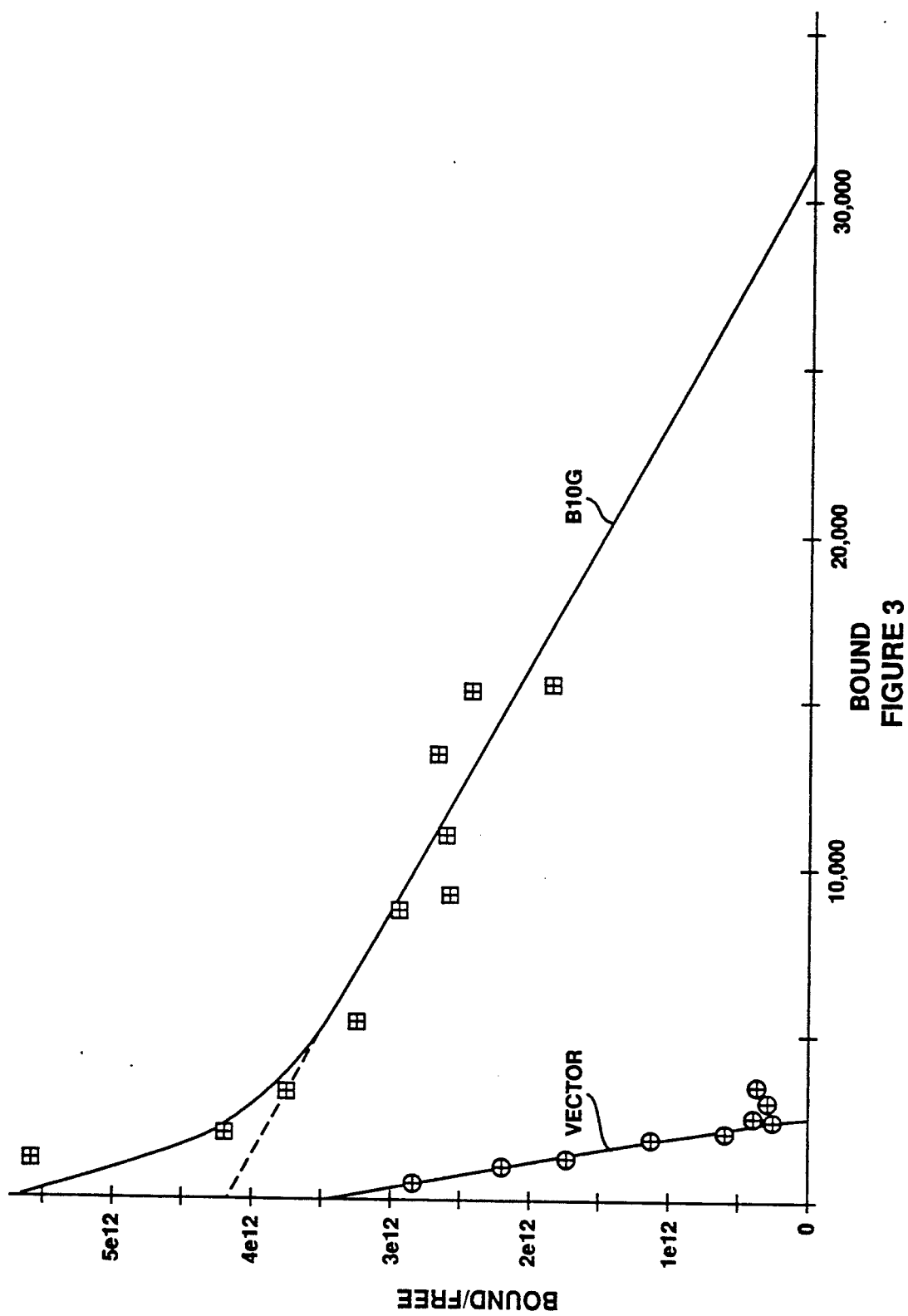
FIG. 3 is a graph depicting low affinity binding of oncostatin M to host cells transfected with a gp130 encoding expression vector, as described in example 2.

The experimental conditions of this assay (the results of which are shown in FIG. 2) were not appropriate for accurate detection of low affinity oncostatin M receptors. Thus, a separate experiment (phthalate oil separation method) was conducted to compare oncostatin M binding by COS-7 cells transfected with B10G alone (no CAV control vector) with oncostatin M binding to non-transfected COS-7 cells. Non-transfected COS-7 cells assayed as a control demonstrated a small number of high affinity oncostatin M receptors ($K_D=3.6 \times 10^{-10}$M). The cells transfected with B10G demonstrated additional low affinity binding of oncostatin M ($K_D=7.7 \times 10^{-9}$M). The results of this oncostatin M binding assay are shown in FIG. 3 as Scatchard transformations of the biological data. The data are reported as the ratio of molecules of $^{125}$I-oncostatin M bound per cell, to free $^{125}$I-oncostatin M molecules (y-axis) versus molecules of $^{125}$I-oncostatin M bound per cell (x-axis). The scale in FIG. 3 differs from that of FIGS. 1 and 2 so that the difference in oncostatin M binding by the gp130-producing cells compared to the control cells can be more readily visualized.

Disorders mediated by oncostatin M thus may be treated by administering gp130 or a fragment thereof. Receptors comprising both gp130 and LIF-R are preferred for use in treating such conditions, however, in view of the higher affinity of such receptors for oncostatin M compared to the affinity of gp130 alone for oncostatin M. gp130 also may be employed as an oncostatin M-binding reagent in diagnostic and research assays.

EXAMPLE 3

Preparation of a Recombinant Fusion Protein Designated LIF-R-Linker-gp130

A recombinant receptor protein of the present invention is prepared by the following procedure. The receptor comprises an LIF-R fragment at the N-terminus attached to a gp130 fragment through a polypeptide linker. The polypeptide linker is of the formula (Gly$_4$Ser)$_8$. An oligonucleotide encoding a portion of the linker sequence, i.e., the sequence Ser(Gly$_4$Ser)$_6$Gly is synthesized by any of the conventional known procedures for oligonucleotide synthesis. The DNA and encoded amino acids sequences of the double-stranded oligonucleotide are as follows:

SEQ ID NO: 7
Bam HI

```
5'  GATCC GGT GGA GGT GGT TCT GGT GGA GGT GGT TCA GGT GGT GGA GGA TCA
3'     G CCT CCT CCA CCA AGA CCA CCT CCA CCA AGT CCA CCA CCT CCT AGT
         Ser Gly Gly Gly Gly Ser Gly Gly Gly Gly Ser Gly Gly Gly Gly Ser

BspMII   XbaI
    GGA GGT GGT GGA TCA GGT GGA GGA GGT TCT GGA GGT GGA GGT TCC GGA T   3'
    CCT CCA CCA CCT AGT CCA CCT CCT CCA AGA CCT CCA CCT CCA AGG CCT AGATC 5'
    Gly Gly Gly Gly Ser Gly Gly Gly Gly Ser Gly Gly Gly Gly Ser Gly
```

The remaining portion of the linker is added during vector construction as described below. This oligonucleotide as well as those discussed below may be synthesized on an automated DNA synthesis machine such as those available from Biosearch, Inc., San Rafael, Calif. or Applied Biosystems.

The linker encoding oligonucleotide is cloned into a vector that preferably contains multiple restriction endonuclease cleavage sites that may be employed for inserting the sequences encoding LIF-R and gp130 on either side of, and in the same reading frame as, the sequence encoding the linker. One such vector is designated pBLUESCRIPT SK ® which is available from Stratagene Cloning Systems, La Jolla, Calif. This plasmid vector is replicable in *E. coli* and contains a polylinker segment that includes 21 unique restriction sites. The plasmid is digested with the restriction enzymes BamHI and XbaI and the linker-encoding oligonucleotide is ligated into the vector using conventional techniques. A recombinant vector containing the inserted oligonucleotide sequence is identified by restriction endonuclease analysis and sizing by gel electrophoresis. A DNA sequence encoding LIF-R is inserted into the pBLUESCRIPT SK ® vector upstream of the linker-encoding oligonucleotide and a DNA sequence encoding gp130 is inserted downstream of the linker sequence. cDNA molecules encoding soluble fragments of LIF-R and gp130 were isolated and amplified using the well known polymerase chain reaction (PCR) procedure. The following oligonucleotides were synthesized for use in the PCR procedures:

SEQ ID NO: 8    (Oligonucleotide No. 1)
                SalI
5' GATAT GTCGAC GATGATGGATATTTACGTATGTTTG 3'

SEQ ID NO: 9    (Oligonucleotide No. 2)
3' CATACATACACCACTGTTTCCTTTTAAGACCTCCTCCA CCTAGG TACG 5'
                                              BamHI SEQ ID NO: 10        (Oligonucleotide No. 3)
           BspMII
5'  CGCGTCCGGAGGAGGTGGATCTGAACTTCTAGATCCATGTGGTTATATC  3'

SEQ ID No. 11        (Oligonucleotide No. 4)
3'  CAAACGAGTTCCTCTTTAACTTATCCGCCGGCGTACG  5'

Oligonucleotides 1 and 2 are used in a PCR reaction to isolate a soluble fragment of LIF-R. The template employed in the reaction is the human LIF-R cDNA cloned as described by Gearing et al. supra. The DNA and encoded amino acid sequences of the cDNA clone are represented in SEQ ID NO: 5. The cloning vector which contains this human LIF-R cDNA clone was deposited in *E. coli* host cells with the American Type Culture Collection, Rockville, Md, U.S.A. on Dec. 11, 1990, under the name pHLIFR-65 (ATCC Accession Number 68491). The deposit was made under the conditions of the Budapest Treaty. The 5' primer is oligonucleotide No. 1, which includes a DNA sequence encoding the first 8 amino acids of the signal sequence of LIF-R and also comprises upstream sequences that introduce a Sal 1 restriction endonuclease cleavage site. Oligonucleotide No. 1 is capable of annealing to the (−) strand that is complementary to nucleotides 179–202 of SEQ ID NO: 5. The 3' primer is oligonucleotide No. 2, which contains a sequence complementary to nucleotides 2651–2677 of SEQ ID NO: 5 (i.e., includes anti-sense nucleotides encoding the last nine amino acids of the extracellular domain of LIF-R). Immediately downstream of the LIF-R encoding sequence, oligonucleotide No. 2 contains a sequence encoding (Gly)$_4$ Ser, and also introduces a BamHI restriction endonuclease cleavage site.

A PCR reaction employing oligonucleotides Nos. 1 and 2 thus isolates and amplifies a DNA sequence encoding an LIF-R fragment containing the entire signal sequence and the entire extracellular domain but lacking the transmembrane region and the extracellular domain. The (Gly)$_4$ Ser sequence attached to the 3' terminus of the LIF-R fragment is part of the polypeptide linker in the final construct.

Any suitable PCR procedure may be employed. One such procedure is described in Sarki et al., Science 239:487 (1988). Another is described in *Recombinant DNA Methodology*, Wu et al., eds., Academic Press Inc., San Diego (1989), pp. 189–196. In general, PCR reactions involve combining the 5' and 3' nucleotides with the template DNA and each of the four deoxynucleoside triphosphates in a suitable buffered solution. The solution is heated, (e.g., from 95° to 100° C.) to denature the double-stranded DNA template and is then cooled before addition of a DNA polymerase enzyme. Multiple cycles of the reactions are carried out in order to amplify the desired DNA fragment.

An example of a suitable PCR procedure is as follows. All temperatures are in degrees centigrade. The following PCR reagents are added to a 1.5 ml Eppendorf microfuge tube: 10 μl of 10X PCR buffer (500 mM KCl, 100 mM Tris-HCl, pH 8.3 at 25° C., 25 mM MgCl$_2$, and 1 mg/ml gelatin) (Perkin-Elmer Cetus, Norwalk, Conn.), 10 μl of a 2 mM solution containing each dNTP (2 mM dATP, 2 mM dCTP, 2 mM dGTP and 2 mM dTTP), 2.5 units (0.5 μl of standard 5000 units/ml solution) of Taq DNA polymerase (Perkin-Elmer Cetus), 50 ng of template DNA, 5 μl of a 20 μM solution of each of oligonucleotide primers 1 and 2, and 74.5 μl water to final volume of 100 μl. The final mixture is then overlaid with 100 μl parafin oil. PCR is carried out using a DNA thermal cycler (Ericomp, San Diego, Calif.) by initially denaturing the template at 94° for 90 seconds, reannealing at 55° for 75 seconds and extending the cDNA at 72° for 150 seconds. PCR is carried out for an additional 20 cycles of amplification using a step program (denaturation at 94°, 25 sec; annealing at 55°, 45 sec; extension at 72°, 150 sec.), followed by a 5 minute extension at 72°.

The sample is removed from the parafin oil and DNA extracted by phenolchloroform extraction and spun column chromatography over G-50 (Boehringer Mannheim). A 10 μl aliquot of the extracted DNA is separated by electrophoresis on 1% SeaKem ™ agarose (FMC BioProducts, Rockland, Me.) and stained with ethidium bromide to confirm that the DNA fragment size is consistent with the predicted product.

The PCR-amplified cDNA products are then digested with SalI and BamHI restriction enzymes using standard procedures. The SalI/BamHI restriction fragment is then separated by gel electrophoresis, e.g., on a 1.2% Seaplaque ™ low gelling temperature (LGT) agarose, and the band representing the desired fragment is isolated. The fragment is inserted into a vector encoding the desired fusion protein as described below.

A plasmid vector containing human gp130 cDNA was deposited in *E. coli* strain DH5α host cells with the American Type Culture Collection, Rockville, Md. under the name B10G/pDC303 (DH5α) on Nov. 14, 1991 and assigned ATCC Accession No. 68827. The deposit was made under the conditions of the Budapest Treaty. The DNA and encoded amino acid sequences of this cloned cDNA are shown in SEQ ID NO: 1.

Oligonucleotides 3 and 4 are employed in the polymerase chain reaction procedure to amplify and isolate a DNA fragment encoding Ser(Gly)$_4$ Ser followed by amino acids 1 to 597 of SEQ ID NO: 1 (the entire extracellular domain of the mature gp130 protein). The 5' primer, oligonucleotide No. 3, includes nucleotides 310 to 336 of SEQ ID NO: 1, which encode the first nine amino acids of the mature gp130 protein. This nucleotide sequence is capable of annealing to the (−) strand that is complementary to nucleotides 310 to 336 of SEQ ID NO: 1. Oligonucleotide No. 3 also encodes a Ser(-Gly)$_4$ Ser sequence directly upstream of (and in the same reading frame as) the gp130 sequence, and further positions a BspMII restriction endonuclease cleavage site near the 5' terminus of the Ser(Gly)$_4$ Ser-encoding sequence.

The 3' primer, oligonucleotide No. 4, includes a sequence complimentary to nucleotides 2080 to 2100 of SEQ ID NO: 1, i.e., includes anti-sense nucleotides encoding the last seven amino acids of the gp130 extracellular domain. Oligonucleotide No. 4 positions a stop codon immediately after the gp130 sequence and also inserts a NotI restriction site downstream. Following amplification of the gp130 fragment by PCR, the PCR reaction products are digested with BspMII and NotI and the desired fragment is isolated.

The above-described LIF-R, Ser(Gly₄Ser)₆Gly linker, and gp130 encoding fragments are assembled into a single DNA sequence as follows. The Ser(Gly₄-Ser)₆Gly linker fragment is excised from the pBLUESCRIPT SK ® vector by digestion with BamHI and BspMII. The linker fragment is then ligated to the 3' end of the LIF-R fragment (cleaved at its 3' terminus after the Gly₄Ser sequence with BamHI). The ligation is conducted under conventional conditions. The 3' end of the linker fragment is ligated to the BspMII-cleaved 5' end of the gp130 fragment. The resulting DNA fragment encodes a receptor of the present invention comprising (from 5' to 3') the signal sequence and extracellular domain of LIF-R attached to a (Gly₄Ser)₈ polypeptide linker which is attached to the mature coding sequence of the gp130 extracellular domain.

This DNA fragment may be inserted into any suitable cloning and/or expression vector. For example, the pBLUESCRIPT SK ® vector may be digested with SalI and NotI and the ligated DNA fragment inserted therein. *E. coli* cells are then transformed with the recombinant vector by conventional procedures.

In an alternative procedure, the pBLUESCRIPT SK ® vector containing the Ser(Gly₄Ser)₆Gly linker sequence is digested with SalI and BamHI and the above described LIF-R-encoding fragment is inserted therein. The resulting vector is then digested with BspMII and NotI and the gp130-encoding fragment is then inserted to form the DNA sequence encoding the receptor of the present invention. The cloned receptor-encoding DNA fragment may be excised and inserted into any suitable expression vector (chosen according to the type of host cell that is desired) using conventional procedures. Host cells transformed with the recombinant expression vector are cultivated to produce the receptor protein. Mammalian host wells are generally preferred for producing the recombinant receptor fusion proteins of the present invention.

The receptor-encoding construct may be excised by SalI and NotI digestion and inserted into a vector suitable for use in mammalian host cells. One suitable vector is designated pDC406. cDNA molecules inserted at the SalI site of this vector are transcribed and translated using regulatory elements derived from HIV and adenovirus. pDC406 contains origins of replication derived from SV40, Epstein-Barr virus and pBR322. The pDC406 vector into which interleukin-1 receptor cDNA has been deposited with the American Type Culture Collection, Rockville, Md. USA under accession number CRL10478. The interleukin-1 receptor cDNA may be excised from the vector using conventional techniques and replaced with the receptor encoding DNA of the present invention prepared above. pDC406 is a derivative of HAV-EO described by Dower et al., *J. Immunol*, 142:4314 (1989). pDC406 differs from HAV-EO by the deletion of the intron present in the adenovirus 2 tripartite leader sequence in HAV-EO.

Examples of suitable mammalian cells for expressing a receptor fusion protein include CV-1 cells (ATCC CCL70) and COS-7 cells, (ATCC CRL 1651) both derived from monkey kidney. Another monkey kidney cell line CV-1/EBNA (ATCC CRL 10478) was derived by transfection of the CV-1 cell line with a gene encoding Epstein-Barr virus nuclear antigen-1 (EBNA-1) and with a vector containing CMV regulatory sequences. See McMahan et al., *EMBO J.* 10:2821 (1991). The EBNA-1 gene allows for episomal replication of expression vectors, such as HAV-EO or pDC406, that contain the EBV origin of replication.

EXAMPLE 4

Preparation of a Recombinant Receptor Fusion Protein Designated gp130-Linker-LIF-R This receptor of the present invention differs from that of Example 3 in that the LIF-R polypeptide (which was the 5' polypeptide in the receptor of Example 3) is now the 3' polypeptide. The following oligonucleotides were synthesized for use in preparing the fusion protein:

SEQ ID NO: 12
5' GATATGTCGACAAGATGTTGACGTTGCAGACTTGG 3'   (oligonucleotide no. 5)

SEQ ID NO: 13
3' CAAACGAGTTCCTCTTTAACTTCCTCCTCCACCTAGGTACG 5'   (oligonucleotide no. 6)

SEQ ID NO: 14
5' CGCGTCCGGAGGAGGTGGTAGCCAGAAAAAGGGGGCTCCTCATG 3'   (oligonucleotide no. 7)

SEQ ID NO: 15
3' CATACATACACCACTGTTTCCTTTTAAGAATCGCCGGCGTACG 5'   (oligonucleotide no. 8)

Oligonucleotides 5 and 6 are employed in a polymerase chain reaction procedure to isolate a fragment of gp130. The 5' primer (oligonucleotide number 5) includes nucleotides 244 to 264 of SEQ ID NO: 1, (the sequence encoding the first seven amino acids of the gp130 signal sequence). Oligonucleotide number 5 also includes a sequence that introduces an upstream SalI site. This nucleotide sequence is capable of annealing to the (−) strand that is complementary to nucleotides 244 to 264 of SEQ ID NO: 1. The 3' primer (oligonucleotide number 6) includes a sequence complementary to nucleotides 2080 to 2100 of SEQ ID NO: 1, i.e. includes antisense nucleotides encoding the last seven amino acids of the gp130 extracellular domain. Oligonucleotide number 6 also encodes a Gly₄Ser sequence immediately 3' to (and in phase with) the gp130 sequence, and also inserts a downstream BamHI site.

A PCR reaction is conducted as described in Example 3 but employing oligonucleotides 5 and 6 on the gp130 cDNA template. A DNA sequence encoding a gp130 fragment that includes the 5' signal sequence and the entire extracellular domain, but none of the transmembrane region or the cytoplasmic domain, is isolated by the PCR reaction. A Gly₄Ser sequence is fused to the 3' terminus of the gp130 fragment. The PCR reaction products are digested with SalI and BamHI and the desired fragment is isolated.

An LIF-R fragment is isolated and amplified by a PCR reaction employing oligonucleotides 7 and 8. The 5' primer (oligonucleotide number 7) includes nucleotides 311 to 331 of SEQ ID NO: 5, which encode the first seven amino acids of the mature LIF-R protein.

This nucleotide sequence is capable of annealing to the (−) strand complementary to nucleotides 311 to 331 of SEQ ID NO: 5. Oligonucleotide number 7 also encodes a Gly$_4$Ser sequence fused to the 5' end of the LIF-R sequence, and inserts an upstream BspMII site. The 3' primer (oligonucleotide number 8) is complementary to nucleotides 2651 to 2677 of SEQ ID NO: 5 (which encode the last nine amino acids of the LIF-R extracellular domain.) Oligonucleotide number 8 also adds a stop codon at the 3' end of the LIF-R sequence, and inserts a Not I site downstream. The PCR reaction products are digested with BspMII and NotI and the desired fragment is isolated.

A DNA sequence encoding the desired receptor protein is prepared by ligating the BamHI site of the gp130 fragment prepared above to the BamHI site at the 5' terminus of the linker fragment described in Example 3. Likewise the C-terminus of the linker encoding fragment is ligated at the BspMII site to the complementary site of the LIF-R encoding fragment prepared above. The resulting DNA fragment may be cloned into an expression vector using procedures described in Example 3. The receptor encoded by the isolated DNA fragment comprises (from the N-terminus to the C-terminus) the signal sequence and extracellular domain of gp130 attached to a (Gly$_4$Ser)$_8$ polypeptide linker which is attached to the mature coding sequence of the LIF-R extracellular domain.

EXAMPLE 5

Receptor Fusion Protein Comprising LIF-R Attached to gp-130 Through An Fc Polypeptide Linker A receptor prepared in accordance with the following procedures is depicted in FIG. 4. The following oligonucleotides were synthesized for use in preparing the receptor fusion protein:

SEQ ID NO: 16
3' CATACATACACCACTGTTTCCTTTTAAGACTCGGGTCTAGATACG 5' (oligonucleotide no. 9)

SEQ ID NO: 17
3' CAAACGAGTTCCTCTTTAACTTCTCGGGTCTAGATACG 5' (oligonucleotide no. 10)

An LIF-R encoding DNA sequence is isolated and amplified in a PCR reaction using oligonucleotides 1 and 9. Oligonucleotide number 1 (the 5' primer) inserts an upstream SalI site and has been described in Example 3. The 3' primer is oligonucleotide number 9 which includes a sequence complementary to nucleotides 2651 to 2677 of SEQ ID NO: 5, i.e., includes antisense nucleotides encoding the last nine amino acids of the extracellular domain of LIF-R. Oligonucleotide number 9 also inserts a downstream BglII site. The PCR reaction products are digested with SalI and BglII, and the desired LIF-R encoding DNA fragment is isolated by gel electrophoresis using conventional procedures. Due to the presence of an internal BglII site in the LIF-R sequence, the BglII digestion should be carried out under conditions that effect partial digestion.

A gp130 encoding DNA fragment is isolated and amplified by PCR reaction using oligonucleotides 5 and 10. The 5' primer (oligonucleotide number 5) inserts an upstream SalI site and has been described above in Example 4. The 3' primer is oligonucleotide number 10, which includes a sequence complementary to nucleotides 2080 to 2100 of SEQ ID NO: 1, i.e., includes antisense nucleotides encoding the last seven amino acids of the gp130 extracellular domain. Oligonucleotide number 10 also inserts a downstream BglII site. The PCR reaction products are digested with SalI and BglII, and the desired gp130 encoding DNA fragment is isolated by gel electrophoresis using conventional techniques.

cDNA encoding a single chain polypeptide derived from the Fc region of a human IgG1 antibody has been cloned into the above-described pBLUESCRIPT SK ® vector to produce a recombinant vector designated hIgG1Fc. A unique BglII site is positioned near the 5' end of the inserted Fc encoding sequence. An SpeI site is immediately downstream of the stop codon. The DNA and encoded amino acid sequences of the cloned Fc cDNA are presented in SEQ ID NO: 3 and SEQ ID NO: 4.

The Fc polypeptide encoded by the cDNA extends from the N-terminal hinge region to the native C-terminus, i.e., is an essentially full-length antibody Fc region. Fc fragments, e.g., those that are truncated at the C-terminal end, also may be employed. The fragments should contain multiple cysteine residues (at least the cysteine residues in the hinge reaction). The antibody from which the Fc polypeptide is derived is preferably of the same species as the patient to be treated with the fusion protein prepared therefrom.

Plasmid hIgG1Fc is digested with BglII and SalI and the BglII/SalI LIF-R fragment prepared above is ligated into the vector by conventional techniques. The Fc encoding sequence is positioned downstream of, and in the same reading frame as, the LIF-R sequence. In a separate reaction, the above-described SalI/BglII fragment of gp130 is also inserted into the same vector. Plasmid vectors containing the desired DNA insert are identified by restriction endonuclease digestion analysis, using convention techniques.

The cloned DNA segment encoding the LIF-R-Fc fusion polypeptide may be excised from the pBLUESCRIPT SK ® vector by digestion with SalI and NotI. Likewise, the DNA segment encoding the gp130-Fc fusion polypeptide may be excised by SalI/NotI digestion. Each excised DNA segment is inserted into an appropriate expression vector, depending on the type of host cell that is desired. One suitable expression vector is the plasmid pDC406, which may be transformed into mammalian host cells as described in Example 3.

In one embodiment of the invention, an expression vector encoding the LIF-R-Fc fusion and a second expression vector encoding the gp130-Fc fusion are co-transfected into the desired host cells. Two separate recombinant polypeptides are thus produced in the host cells. The first polypeptide comprises the Fc polypeptide fused in frame to the C-terminus of the gp130 fragment. The second polypeptide comprises the Fc polypeptide fused in frame to the C-terminus of the LIF-R fragment. Disulfide bonds that form between the two Fc regions covalently link the two separate fusion polypeptides into a receptor protein of the present invention.

Alternatively, the LIF-R-Fc and gp130-Fc polypeptides may be separately transformed into host cells (as opposed to co-transfection into the same host cell). The two polypeptides are purified from the host cells and then combined in a suitable buffered solution, whereupon interchain disulfide bonds form between the two Fc regions.

The receptor protein may be purified using any of a number of conventional protein purification techniques. Since antibody Fc regions bind to protein A and protein G, affinity chromatography employing protein A or protein G attached to an insoluble support material may be employed in the purification process. In one procedure, one liter culture supernatant containing the receptor is passed over a solid phase protein G column, and the column is then washed thoroughly with phosphate-buffered saline (PBS). The adsorbed Fc-containing fusion protein is eluted with 50 mM glycine buffer, pH 3 and brought to pH 7 with 2M Tris buffer, pH 9. Further purification may involve immunoaffinity column(s), e.g., affinity columns having LIF or OSM bound thereto

EXAMPLE 6

Preparation of Monoclonal Antibodies Directed against a Receptor

Preparations of a purified receptor protein of the present invention, or transfected COS cells expressing high levels of the receptor, are employed to generate monoclonal antibodies against the receptor using conventional techniques, for example, those disclosed in U.S. Pat. No. 4,411,993. To immunize mice, a receptor immunogen is emulsified in complete Freund's adjuvant and injected subcutaneously in amounts ranging from 10–100 μg into Balb/c mice. Ten to twelve days later, the immunized animals are boosted with additional immunogen emulsified in incomplete Freund's adjuvant and periodically boosted thereafter on a weekly to bi-weekly immunization schedule. Serum samples are periodically taken by retro-orbital bleeding or tail-tip excision for testing by dot-blot assay (antibody sandwich) or ELISA (enzyme-linked immunosorbent assay). Other assay procedures are also suitable. Following detection of an appropriate antibody titer, positive animals are given an intravenous injection of antigen in saline. Three to four days later, the animals are sacrificed, splenocytes harvested, and fused to the murine myeloma cell line NS1. Hybridoma cell lines generated by this procedure are plated in multiple microtiter plates in a HAT selective medium (hypoxantine, aminopterin, and thymidine) to inhibit proliferation of non-fused cells, myeloma hybrids, and spleen cell hybrids.

Hybridoma clones thus generated can be screened by ELISA for reactivity with the receptor protein, for example, by adaptations of the techniques disclosed by Engvall et al., *Immunochem* 8.871 (1971) and in U.S. Pat. No. 4,704,004. Positive clones are then injected into the peritoneal cavities of syngeneic Balb/c mice to produce ascites containing high concentrations (greater than 1 mg/ml) of anti-receptor monoclonal antibody. The resulting monoclonal antibody can be purified by ammonium sulfate precipitation followed by gel exclusion chromatography, and/or affinity chromatography based on binding of antibody to Protein A of *Staphylococcus aureus*.

BRIEF DESCRIPTION OF THE SEQUENCE LISTING

SEQ ID NO: 1 and SEQ ID NO: 2 present the DNA sequence and encoded amino acid sequence for cloned cDNA encoding an N-terminal fragment of gp130.

SEQ ID NO: 3 and SEQ ID NO: 4 present the DNA sequence and encoded amino acid sequence for cloned cDNA encoding a polypeptide that corresponds to the Fc region of an IgG1 antibody.

SEQ ID NO: 5 and SEQ ID NO: 6 present the DNA sequence and encoded amino acid sequence for cloned cDNA encoding an N-terminal fragment of LIF-R.

SEQ ID NO: 7 presents the DNA sequence of the coding strand of a chemically synthesized DNA molecule encoding a polypeptide linker used in constructing certain receptors of the present invention.

SEQ ID NO: 8–SEQ ID NO: 17 present the DNA sequence of various single-stranded oligonucleotide primers employed in polymerase chain reactions to construct certain receptors of the present invention.

---

What is claimed is:

1. A receptor capable of binding oncostatin M and leukemia inhibitory factor, comprising gp130 covalently linked to LIF-R,
    wherein said gp130 is encoded by a gp130-encoding DNA selected from the group consisting of DNA encoding the amino acid sequence presented in SEQ ID NO: 2 and DNA capable of hybridizing under moderately stringent conditions to the complement of DNA encoding the amino acid sequence presented in SEQ ID NO: 2, wherein said gp130-encoding DNA encodes a biologically active gp130 polypeptide; and
    wherein said LIF-R is encoded by a LIF-R-encoding DNA selected from the group consisting of DNA encoding the amino acid sequence presented in SEQ ID NO: 6 and DNA capable of hybridizing under moderately stringent conditions to the complement of DNA encoding the amino acid sequence presented in SEQ ID NO: 6, wherein said LIF-R-encoding DNA encodes a biologically active LIF-R polypeptide.

2. A receptor according to claim 1, wherein said receptor comprises a soluble gp130 polypeptide covalently linked to a soluble LIF-R polypeptide.

3. A receptor capable of binding oncostatin M and leukemia inhibitory factor, wherein said receptor comprises gp130 covalently linked to LIF-R via a polypeptide linker,
    wherein said gp130 is encoded by a gp130-encoding DNA selected from the group consisting of DNA encoding the amino acid sequence presented in SEQ ID NO: 2 and DNA capable of hybridizing under moderately stringent conditions to the complement of DNA encoding the amino acid sequence presented in SEQ ID NO: 2, wherein said gp130-encoding DNA encodes a biologically active gp130 polypeptide; and
    wherein said LIF-R is encoded by a LIF-R-encoding DNA selected from the group consisting of DNA encoding the amino acid sequence presented in SEQ ID NO: 6 and DNA capable of hybridizing under moderately stringent conditions to the complement of DNA encoding the amino acid sequence presented in SEQ ID NO: 6, wherein said LIF-R-encoding DNA encodes a biologically active LIF-R polypeptide.

4. A receptor according to claim 3, wherein said receptor is a recombinant fusion protein of the formula:

$$R_1\text{-}L\text{-}R_2 \text{ or } R_2\text{-}L\text{-}R_1$$

wherein $R_1$ represents gp130; $R_2$ represents LIF-R; and L represents a polypeptide linker.

5. A receptor according to claim 4 wherein the polypeptide linker comprises from 20 to 100 amino acids selected from the group consisting of glycine, asparagine, serine, threonine, and alanine.

6. A receptor according to claim 5 wherein the polypeptide linker comprises an amino acid sequence selected from the group consisting of: $(Gly_4\text{-}Ser\text{-}Gly_5\text{-}Ser)_2$ and $(Gly_4\text{-}Ser)_n$, wherein n is 4–12.

7. A receptor according to claim 3, comprising a first fusion polypeptide that comprises an antibody Fc region polypeptide attached to the C-terminus of a soluble gp130 polypeptide, and a second fusion polypeptide that comprises an antibody Fc region polypeptide attached to the C-terminus of a soluble LIF-R polypeptide, wherein said first fusion polypeptide is linked to said second fusion polypeptide via disulfide bonds between the Fc region polypeptides.

8. A purified receptor comprising gp130 non-covalently linked to LIF-R,
    wherein said gp130 is encoded by a gp130-encoding DNA selected from the group consisting of DNA encoding the amino acid sequence presented in SEQ ID NO: 2 and DNA capable of hybridizing under moderately stringent conditions to the complement of DNA encoding the amino acid sequence presented in SEQ ID NO: 2, wherein said gp130-encoding DNA encodes a biologically active gp130 polypeptide; and
    wherein said LIF-R is encoded by a LIF-R-encoding DNA selected from the group consisting of DNA encoding the amino acid sequence presented in SEQ ID NO: 6 and DNA capable of hybridizing under moderately stringent conditions to the complement of DNA encoding the amino acid sequence presented in SEQ ID NO: 6, wherein said LIF-R-encoding DNA encodes a biologically active LIF-R polypeptide.

9. A pharmaceutical composition comprising the receptor of claim 1 and a suitable diluent or carrier.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
            ( A ) LENGTH: 2369 base pairs
            ( B ) TYPE: nucleic acid
            ( C ) STRANDEDNESS: single
            ( D ) TOPOLOGY: linear ( i i ) MOLECULE TYPE: cDNA to mRNA ( i i i ) HYPOTHETICAL: NO ( i v ) ANTI-SENSE: NO ( v ) FRAGMENT TYPE: N-terminal ( v i ) ORIGINAL SOURCE:
            ( F ) TISSUE TYPE: human placenta ( v i i ) IMMEDIATE SOURCE:
            ( B ) CLONE: B10G/pDC303

( i x ) FEATURE:

( A ) NAME/KEY: CDS
( B ) LOCATION: 244..2369

( i x ) FEATURE:
( A ) NAME/KEY: matpeptide
( B ) LOCATION: 310..2369

( i x ) FEATURE:
( A ) NAME/KEY: sigpeptide
( B ) LOCATION: 244..309

( x i ) SEQUENCE DESCRIPTION: SEQ ID NO:1:

| | | | | |
|---|---|---|---|---|
| GGCCCGCGGA | GTCGCGCTGG | GCCGCCCCGG | CGCAGCTGAA | CCGGGGGCCG | CGCCTGCCAG | 60 |
| GCCGACGGGT | CTGGCCCAGC | CTGGCGCCAA | GGGGTTCGTG | CGCTGTGGAG | ACGCGGAGGG | 120 |
| TCGAGGCGGC | GCGGCCTGAG | TGAAACCCAA | TGGAAAAAGC | ATGACATTTA | GAAGTAGAAG | 180 |
| ACTTAGCTTC | AAATCCCTAC | TCCTTCACTT | ACTAATTTTG | TGATTTGGAA | ATATCCGCGC | 240 |

```
AAG ATG TTG ACG TTG CAG ACT TGG CTA GTG CAA GCC TTG TTT ATT TTC      288
    Met Leu Thr Leu Gln Thr Trp Leu Val Gln Ala Leu Phe Ile Phe
    -22     -20                     -15                 -10

CTC ACC ACT GAA TCT ACA GGT GAA CTT CTA GAT CCA TGT GGT TAT ATC      336
Leu Thr Thr Glu Ser Thr Gly Glu Leu Leu Asp Pro Cys Gly Tyr Ile
        -5                      1                   5

AGT CCT GAA TCT CCA GTT GTA CAA CTT CAT TCT AAT TTC ACT GCA GTT      384
Ser Pro Glu Ser Pro Val Val Gln Leu His Ser Asn Phe Thr Ala Val
 10              15                  20                  25

TGT GTG CTA AAG GAA AAA TGT ATG GAT TAT TTT CAT GTA AAT GCT AAT      432
Cys Val Leu Lys Glu Lys Cys Met Asp Tyr Phe His Val Asn Ala Asn
             30              35                  40

TAC ATT GTC TGG AAA ACA AAC CAT TTT ACT ATT CCT AAG GAG CAA TAT      480
Tyr Ile Val Trp Lys Thr Asn His Phe Thr Ile Pro Lys Glu Gln Tyr
             45                  50              55

ACT ATC ATA AAC AGA ACA GCA TCC AGT GTC ACC TTT ACA GAT ATA GCT      528
Thr Ile Ile Asn Arg Thr Ala Ser Ser Val Thr Phe Thr Asp Ile Ala
         60              65                  70

TCA TTA AAT ATT CAG CTC ACT TGC AAC ATT CTT ACA TTC GGA CAG CTT      576
Ser Leu Asn Ile Gln Leu Thr Cys Asn Ile Leu Thr Phe Gly Gln Leu
 75              80                  85

GAA CAG AAT GTT TAT GGA ATC ACA ATA ATT TCA GGC TTG CCT CCA GAA      624
Glu Gln Asn Val Tyr Gly Ile Thr Ile Ile Ser Gly Leu Pro Pro Glu
 90              95                 100                 105

AAA CCT AAA AAT TTG AGT TGC ATT GTG AAC GAG GGG AAG AAA ATG AGG      672
Lys Pro Lys Asn Leu Ser Cys Ile Val Asn Glu Gly Lys Lys Met Arg
                110                 115                 120

TGT GAG TGG GAT GGT GGA AGG GAA ACA CAC TTG GAG ACA AAC TTC ACT      720
Cys Glu Trp Asp Gly Gly Arg Glu Thr His Leu Glu Thr Asn Phe Thr
             125                 130                 135

TTA AAA TCT GAA TGG GCA ACA CAC AAG TTT GCT GAT TGC AAA GCA AAA      768
Leu Lys Ser Glu Trp Ala Thr His Lys Phe Ala Asp Cys Lys Ala Lys
         140                 145                 150

CGT GAC ACC CCC ACC TCA TGC ACT GTT GAT TAT TCT ACT GTG TAT TTT      816
Arg Asp Thr Pro Thr Ser Cys Thr Val Asp Tyr Ser Thr Val Tyr Phe
 155                 160                 165

GTC AAC ATT GAA GTC TGG GTA GAA GCA GAG AAT GCC CTT GGG AAG GTT      864
Val Asn Ile Glu Val Trp Val Glu Ala Glu Asn Ala Leu Gly Lys Val
 170             175                 180                 185

ACA TCA GAT CAT ATC AAT TTT GAT CCT GTA TAT AAA GTG AAG CCC AAT      912
Thr Ser Asp His Ile Asn Phe Asp Pro Val Tyr Lys Val Lys Pro Asn
             190                 195                 200

CCG CCA CAT AAT TTA TCA GTG ATC AAC TCA GAG GAA CTG TCT AGT ATC      960
Pro Pro His Asn Leu Ser Val Ile Asn Ser Glu Glu Leu Ser Ser Ile
         205                 210                 215

TTA AAA TTG ACA TGG ACC AAC CCA AGT ATT AAG AGT GTT ATA ATA CTA     1008
```

|     |     |     |     |     |     |     |     |     |     |     |     |     |     |     |     |
|---|---|---|---|---|---|---|---|---|---|---|---|---|---|---|---|
| Leu | Lys | Leu | Thr | Trp | Thr | Asn | Pro | Ser | Ile | Lys | Ser | Val | Ile | Ile | Leu |
|     |     | 220 |     |     |     |     | 225 |     |     |     | 230 |     |     |     |     |

| AAA | TAT | AAC | ATT | CAA | TAT | AGG | ACC | AAA | GAT | GCC | TCA | ACT | TGG | AGC | CAG | 1056 |
|---|---|---|---|---|---|---|---|---|---|---|---|---|---|---|---|---|
| Lys | Tyr | Asn | Ile | Gln | Tyr | Arg | Thr | Lys | Asp | Ala | Ser | Thr | Trp | Ser | Gln |  |
| 235 |     |     |     |     | 240 |     |     |     |     | 245 |     |     |     |     |     |  |

| ATT | CCT | CCT | GAA | GAC | ACA | GCA | TCC | ACC | CGA | TCT | TCA | TTC | ACT | GTC | CAA | 1104 |
|---|---|---|---|---|---|---|---|---|---|---|---|---|---|---|---|---|
| Ile | Pro | Pro | Glu | Asp | Thr | Ala | Ser | Thr | Arg | Ser | Ser | Phe | Thr | Val | Gln |  |
| 250 |     |     |     |     | 255 |     |     |     |     | 260 |     |     |     |     | 265 |  |

| GAC | CTT | AAA | CCT | TTT | ACA | GAA | TAT | GTG | TTT | AGG | ATT | CGC | TGT | ATG | AAG | 1152 |
|---|---|---|---|---|---|---|---|---|---|---|---|---|---|---|---|---|
| Asp | Leu | Lys | Pro | Phe | Thr | Glu | Tyr | Val | Phe | Arg | Ile | Arg | Cys | Met | Lys |  |
|     |     |     |     | 270 |     |     |     |     | 275 |     |     |     |     | 280 |     |  |

| GAA | GAT | GGT | AAG | GGA | TAC | TGG | AGT | GAC | TGG | AGT | GAA | GAA | GCA | AGT | GGG | 1200 |
|---|---|---|---|---|---|---|---|---|---|---|---|---|---|---|---|---|
| Glu | Asp | Gly | Lys | Gly | Tyr | Trp | Ser | Asp | Trp | Ser | Glu | Glu | Ala | Ser | Gly |  |
|     |     |     | 285 |     |     |     |     | 290 |     |     |     |     | 295 |     |     |  |

| ATC | ACC | TAT | GAA | GAT | AGA | CCA | TCT | AAA | GCA | CCA | AGT | TTC | TGG | TAT | AAA | 1248 |
|---|---|---|---|---|---|---|---|---|---|---|---|---|---|---|---|---|
| Ile | Thr | Tyr | Glu | Asp | Arg | Pro | Ser | Lys | Ala | Pro | Ser | Phe | Trp | Tyr | Lys |  |
|     |     | 300 |     |     |     |     | 305 |     |     |     | 310 |     |     |     |     |  |

| ATA | GAT | CCA | TCC | CAT | ACT | CAA | GGC | TAC | AGA | ACT | GTA | CAA | CTC | GTG | TGG | 1296 |
|---|---|---|---|---|---|---|---|---|---|---|---|---|---|---|---|---|
| Ile | Asp | Pro | Ser | His | Thr | Gln | Gly | Tyr | Arg | Thr | Val | Gln | Leu | Val | Trp |  |
| 315 |     |     |     |     | 320 |     |     |     |     | 325 |     |     |     |     |     |  |

| AAG | ACA | TTG | CCT | CCT | TTT | GAA | GCC | AAT | GGA | AAA | ATC | TTG | GAT | TAT | GAA | 1344 |
|---|---|---|---|---|---|---|---|---|---|---|---|---|---|---|---|---|
| Lys | Thr | Leu | Pro | Pro | Phe | Glu | Ala | Asn | Gly | Lys | Ile | Leu | Asp | Tyr | Glu |  |
| 330 |     |     |     |     | 335 |     |     |     |     | 340 |     |     |     |     | 345 |  |

| GTG | ACT | CTC | ACA | AGA | TGG | AAA | TCA | CAT | TTA | CAA | AAT | TAC | ACA | GTT | AAT | 1392 |
|---|---|---|---|---|---|---|---|---|---|---|---|---|---|---|---|---|
| Val | Thr | Leu | Thr | Arg | Trp | Lys | Ser | His | Leu | Gln | Asn | Tyr | Thr | Val | Asn |  |
|     |     |     |     | 350 |     |     |     |     | 355 |     |     |     |     | 360 |     |  |

| GCC | ACA | AAA | CTG | ACA | GTA | AAT | CTC | ACA | AAT | GAT | CGC | TAT | CTA | GCA | ACC | 1440 |
|---|---|---|---|---|---|---|---|---|---|---|---|---|---|---|---|---|
| Ala | Thr | Lys | Leu | Thr | Val | Asn | Leu | Thr | Asn | Asp | Arg | Tyr | Leu | Ala | Thr |  |
|     |     | 365 |     |     |     |     | 370 |     |     |     | 375 |     |     |     |     |  |

| CTA | ACA | GTA | AGA | AAT | CTT | GTT | GGC | AAA | TCA | GAT | GCA | GCT | GTT | TTA | ACT | 1488 |
|---|---|---|---|---|---|---|---|---|---|---|---|---|---|---|---|---|
| Leu | Thr | Val | Arg | Asn | Leu | Val | Gly | Lys | Ser | Asp | Ala | Ala | Val | Leu | Thr |  |
|     |     | 380 |     |     |     |     | 385 |     |     |     | 390 |     |     |     |     |  |

| ATC | CCT | GCC | TGT | GAC | TTT | CAA | GCT | ACT | CAC | CCT | GTA | ATG | GAT | CTT | AAA | 1536 |
|---|---|---|---|---|---|---|---|---|---|---|---|---|---|---|---|---|
| Ile | Pro | Ala | Cys | Asp | Phe | Gln | Ala | Thr | His | Pro | Val | Met | Asp | Leu | Lys |  |
| 395 |     |     |     |     | 400 |     |     |     |     | 405 |     |     |     |     |     |  |

| GCA | TTC | CCC | AAA | GAT | AAC | ATG | CTT | TGG | GTG | GAA | TGG | ACT | ACT | CCA | AGG | 1584 |
|---|---|---|---|---|---|---|---|---|---|---|---|---|---|---|---|---|
| Ala | Phe | Pro | Lys | Asp | Asn | Met | Leu | Trp | Val | Glu | Trp | Thr | Thr | Pro | Arg |  |
| 410 |     |     |     |     | 415 |     |     |     |     | 420 |     |     |     |     | 425 |  |

| GAA | TCT | GTA | AAG | AAA | TAT | ATA | CTT | GAG | TGG | TGT | GTG | TTA | TCA | GAT | AAA | 1632 |
|---|---|---|---|---|---|---|---|---|---|---|---|---|---|---|---|---|
| Glu | Ser | Val | Lys | Lys | Tyr | Ile | Leu | Glu | Trp | Cys | Val | Leu | Ser | Asp | Lys |  |
|     |     |     | 430 |     |     |     |     | 435 |     |     |     |     | 440 |     |     |  |

| GCA | CCC | TGT | ATC | ACA | GAC | TGG | CAA | CAA | GAA | GAT | GGT | ACC | GTG | CAT | CGC | 1680 |
|---|---|---|---|---|---|---|---|---|---|---|---|---|---|---|---|---|
| Ala | Pro | Cys | Ile | Thr | Asp | Trp | Gln | Gln | Glu | Asp | Gly | Thr | Val | His | Arg |  |
|     |     |     | 445 |     |     |     |     | 450 |     |     |     |     | 455 |     |     |  |

| ACC | TAT | TTA | AGA | GGG | AAC | TTA | GCA | GAG | AGC | AAA | TGC | TAT | TTG | ATA | ACA | 1728 |
|---|---|---|---|---|---|---|---|---|---|---|---|---|---|---|---|---|
| Thr | Tyr | Leu | Arg | Gly | Asn | Leu | Ala | Glu | Ser | Lys | Cys | Tyr | Leu | Ile | Thr |  |
|     |     |     | 460 |     |     |     |     | 465 |     |     |     |     | 470 |     |     |  |

| GTT | ACT | CCA | GTA | TAT | GCT | GAT | GGA | CCA | GGA | AGC | CCT | GAA | TCC | ATA | AAG | 1776 |
|---|---|---|---|---|---|---|---|---|---|---|---|---|---|---|---|---|
| Val | Thr | Pro | Val | Tyr | Ala | Asp | Gly | Pro | Gly | Ser | Pro | Glu | Ser | Ile | Lys |  |
| 475 |     |     |     |     | 480 |     |     |     |     | 485 |     |     |     |     |     |  |

| GCA | TAC | CTT | AAA | CAA | GCT | CCA | CCT | TCC | AAA | GGA | CCT | ACT | GTT | CGG | ACA | 1824 |
|---|---|---|---|---|---|---|---|---|---|---|---|---|---|---|---|---|
| Ala | Tyr | Leu | Lys | Gln | Ala | Pro | Pro | Ser | Lys | Gly | Pro | Thr | Val | Arg | Thr |  |
| 490 |     |     |     |     | 495 |     |     |     |     | 500 |     |     |     |     | 505 |  |

| AAA | AAA | GTA | GGG | AAA | AAC | GAA | GCT | GTC | TTA | GAG | TGG | GAC | CAA | CTT | CCT | 1872 |
|---|---|---|---|---|---|---|---|---|---|---|---|---|---|---|---|---|
| Lys | Lys | Val | Gly | Lys | Asn | Glu | Ala | Val | Leu | Glu | Trp | Asp | Gln | Leu | Pro |  |
|     |     |     | 510 |     |     |     |     | 515 |     |     |     |     | 520 |     |     |  |

| GTT | GAT | GTT | CAG | AAT | GGA | TTT | ATC | AGA | AAT | TAT | ACT | ATA | TTT | TAT | AGA | 1920 |
|---|---|---|---|---|---|---|---|---|---|---|---|---|---|---|---|---|
| Val | Asp | Val | Gln | Asn | Gly | Phe | Ile | Arg | Asn | Tyr | Thr | Ile | Phe | Tyr | Arg |  |
|     |     |     | 525 |     |     |     |     | 530 |     |     |     |     | 535 |     |     |  |

| ACC | ATC | ATT | GGA | AAT | GAA | ACT | GCT | GTG | AAT | GTG | GAT | TCT | TCC | CAC | ACA | 1968 |
|---|---|---|---|---|---|---|---|---|---|---|---|---|---|---|---|---|
| Thr | Ile | Ile | Gly | Asn | Glu | Thr | Ala | Val | Asn | Val | Asp | Ser | Ser | His | Thr |  |
|     |     | 540 |     |     |     |     | 545 |     |     |     | 550 |     |     |     |     |  |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| GAA | TAT | ACA | TTG | TCC | TCT | TTG | ACT | AGT | GAC | ACA | TTG | TAC | ATG | GTA | CGA | 2016 |
| Glu | Tyr | Thr | Leu | Ser | Ser | Leu | Thr | Ser | Asp | Thr | Leu | Tyr | Met | Val | Arg |      |
|     | 555 |     |     |     | 560 |     |     |     |     | 565 |     |     |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ATG | GCA | GCA | TAC | ACA | GAT | GAA | GGT | GGG | AAG | GAT | GGT | CCA | GAA | TTC | ACT | 2064 |
| Met | Ala | Ala | Tyr | Thr | Asp | Glu | Gly | Gly | Lys | Asp | Gly | Pro | Glu | Phe | Thr |      |
| 570 |     |     |     | 575 |     |     |     |     | 580 |     |     |     |     | 585 |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| TTT | ACT | ACC | CCA | AAG | TTT | GCT | CAA | GGA | GAA | ATT | GAA | GCC | ATA | GTC | GTG | 2112 |
| Phe | Thr | Thr | Pro | Lys | Phe | Ala | Gln | Gly | Glu | Ile | Glu | Ala | Ile | Val | Val |      |
|     |     |     |     | 590 |     |     |     |     | 595 |     |     |     |     | 600 |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| CCT | GTT | TGC | TTA | GCA | TTC | CTA | TTG | ACA | ACT | CTT | CTG | GGA | GTG | CTG | TTC | 2160 |
| Pro | Val | Cys | Leu | Ala | Phe | Leu | Leu | Thr | Thr | Leu | Leu | Gly | Val | Leu | Phe |      |
|     |     |     | 605 |     |     |     |     | 610 |     |     |     |     | 615 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| TGC | TTT | AAT | AAG | CGA | GAC | CTA | ATT | AAA | AAA | CAC | ATC | TGG | CCT | AAT | GTT | 2208 |
| Cys | Phe | Asn | Lys | Arg | Asp | Leu | Ile | Lys | Lys | His | Ile | Trp | Pro | Asn | Val |      |
|     |     | 620 |     |     |     |     | 625 |     |     |     |     | 630 |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| CCA | GAT | CCT | TCA | AAG | AGT | CAT | ATT | GCC | CAG | TGG | TCA | CCT | CAC | ACT | CCT | 2256 |
| Pro | Asp | Pro | Ser | Lys | Ser | His | Ile | Ala | Gln | Trp | Ser | Pro | His | Thr | Pro |      |
|     | 635 |     |     |     |     | 640 |     |     |     |     | 645 |     |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| CCA | AGG | CAC | AAT | TTT | AAT | TCA | AAA | GAT | CAA | ATG | TAT | TCA | GAT | GGC | AAT | 2304 |
| Pro | Arg | His | Asn | Phe | Asn | Ser | Lys | Asp | Gln | Met | Tyr | Ser | Asp | Gly | Asn |      |
| 650 |     |     |     |     | 655 |     |     |     |     | 660 |     |     |     |     | 665 |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| TTC | ACT | GAT | GTA | AGT | GTT | GTG | GAA | ATA | GAA | GCA | AAT | GAC | AAA | AAG | CCT | 2352 |
| Phe | Thr | Asp | Val | Ser | Val | Val | Glu | Ile | Glu | Ala | Asn | Asp | Lys | Lys | Pro |      |
|     |     |     |     | 670 |     |     |     |     | 675 |     |     |     |     | 680 |     |      |

|     |     |     |     |     |      |
|-----|-----|-----|-----|-----|------|
| TTT | CCA | GAA | GAT | CTG | AA 2369 |
| Phe | Pro | Glu | Asp | Leu |      |
|     |     |     | 685 |     |      |

( 2 ) INFORMATION FOR SEQ ID NO:2:

( i ) SEQUENCE CHARACTERISTICS:
        ( A ) LENGTH: 708 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Leu | Thr | Leu | Gln | Thr | Trp | Leu | Val | Gln | Ala | Leu | Phe | Ile | Phe | Leu |
|-----|-----|-----|-----|-----|-----|-----|-----|-----|-----|-----|-----|-----|-----|-----|-----|
| -22 |     | -20 |     |     |     | -15 |     |     |     |     | -10 |     |     |     |     |

| Thr | Thr | Glu | Ser | Thr | Gly | Glu | Leu | Leu | Asp | Pro | Cys | Gly | Tyr | Ile | Ser |
|-----|-----|-----|-----|-----|-----|-----|-----|-----|-----|-----|-----|-----|-----|-----|-----|
|     | -5  |     |     |     |     | 1   |     |     |     | 5   |     |     |     |     | 10  |

| Pro | Glu | Ser | Pro | Val | Val | Gln | Leu | His | Ser | Asn | Phe | Thr | Ala | Val | Cys |
|-----|-----|-----|-----|-----|-----|-----|-----|-----|-----|-----|-----|-----|-----|-----|-----|
|     |     |     |     |     | 15  |     |     |     |     | 20  |     |     |     |     | 25  |

| Val | Leu | Lys | Glu | Lys | Cys | Met | Asp | Tyr | Phe | His | Val | Asn | Ala | Asn | Tyr |
|-----|-----|-----|-----|-----|-----|-----|-----|-----|-----|-----|-----|-----|-----|-----|-----|
|     |     |     | 30  |     |     |     |     | 35  |     |     |     |     | 40  |     |     |

| Ile | Val | Trp | Lys | Thr | Asn | His | Phe | Thr | Ile | Pro | Lys | Glu | Gln | Tyr | Thr |
|-----|-----|-----|-----|-----|-----|-----|-----|-----|-----|-----|-----|-----|-----|-----|-----|
|     |     |     | 45  |     |     |     |     | 50  |     |     |     |     | 55  |     |     |

| Ile | Ile | Asn | Arg | Thr | Ala | Ser | Ser | Val | Thr | Phe | Thr | Asp | Ile | Ala | Ser |
|-----|-----|-----|-----|-----|-----|-----|-----|-----|-----|-----|-----|-----|-----|-----|-----|
|     |     | 60  |     |     |     |     | 65  |     |     |     |     | 70  |     |     |     |

| Leu | Asn | Ile | Gln | Leu | Thr | Cys | Asn | Ile | Leu | Thr | Phe | Gly | Gln | Leu | Glu |
|-----|-----|-----|-----|-----|-----|-----|-----|-----|-----|-----|-----|-----|-----|-----|-----|
| 75  |     |     |     |     | 80  |     |     |     |     | 85  |     |     |     |     | 90  |

| Gln | Asn | Val | Tyr | Gly | Ile | Thr | Ile | Ile | Ser | Gly | Leu | Pro | Pro | Glu | Lys |
|-----|-----|-----|-----|-----|-----|-----|-----|-----|-----|-----|-----|-----|-----|-----|-----|
|     |     |     |     | 95  |     |     |     |     | 100 |     |     |     |     | 105 |     |

| Pro | Lys | Asn | Leu | Ser | Cys | Ile | Val | Asn | Glu | Gly | Lys | Lys | Met | Arg | Cys |
|-----|-----|-----|-----|-----|-----|-----|-----|-----|-----|-----|-----|-----|-----|-----|-----|
|     |     |     | 110 |     |     |     |     | 115 |     |     |     |     | 120 |     |     |

| Glu | Trp | Asp | Gly | Gly | Arg | Glu | Thr | His | Leu | Glu | Thr | Asn | Phe | Thr | Leu |
|-----|-----|-----|-----|-----|-----|-----|-----|-----|-----|-----|-----|-----|-----|-----|-----|
|     |     | 125 |     |     |     |     | 130 |     |     |     |     | 135 |     |     |     |

| Lys | Ser | Glu | Trp | Ala | Thr | His | Lys | Phe | Ala | Asp | Cys | Lys | Ala | Lys | Arg |
|-----|-----|-----|-----|-----|-----|-----|-----|-----|-----|-----|-----|-----|-----|-----|-----|
|     | 140 |     |     |     |     | 145 |     |     |     |     | 150 |     |     |     |     |

```
Asp Thr Pro Thr Ser Cys Thr Val Asp Tyr Ser Thr Val Tyr Phe Val
155             160             165             170

Asn Ile Glu Val Trp Val Glu Ala Glu Asn Ala Leu Gly Lys Val Thr
                175             180             185

Ser Asp His Ile Asn Phe Asp Pro Val Tyr Lys Val Lys Pro Asn Pro
            190             195             200

Pro His Asn Leu Ser Val Ile Asn Ser Glu Glu Leu Ser Ser Ile Leu
        205             210             215

Lys Leu Thr Trp Thr Asn Pro Ser Ile Lys Ser Val Ile Ile Leu Lys
    220             225             230

Tyr Asn Ile Gln Tyr Arg Thr Lys Asp Ala Ser Thr Trp Ser Gln Ile
235             240             245             250

Pro Pro Glu Asp Thr Ala Ser Thr Arg Ser Ser Phe Thr Val Gln Asp
            255             260             265

Leu Lys Pro Phe Thr Glu Tyr Val Phe Arg Ile Arg Cys Met Lys Glu
        270             275             280

Asp Gly Lys Gly Tyr Trp Ser Asp Trp Ser Glu Glu Ala Ser Gly Ile
    285             290             295

Thr Tyr Glu Asp Arg Pro Ser Lys Ala Pro Ser Phe Trp Tyr Lys Ile
300             305             310

Asp Pro Ser His Thr Gln Gly Tyr Arg Thr Val Gln Leu Val Trp Lys
315             320             325             330

Thr Leu Pro Pro Phe Glu Ala Asn Gly Lys Ile Leu Asp Tyr Glu Val
            335             340             345

Thr Leu Thr Arg Trp Lys Ser His Leu Gln Asn Tyr Thr Val Asn Ala
        350             355             360

Thr Lys Leu Thr Val Asn Leu Thr Asn Asp Arg Tyr Leu Ala Thr Leu
    365             370             375

Thr Val Arg Asn Leu Val Gly Lys Ser Asp Ala Ala Val Leu Thr Ile
380             385             390

Pro Ala Cys Asp Phe Gln Ala Thr His Pro Val Met Asp Leu Lys Ala
395             400             405             410

Phe Pro Lys Asp Asn Met Leu Trp Val Glu Trp Thr Thr Pro Arg Glu
            415             420             425

Ser Val Lys Lys Tyr Ile Leu Glu Trp Cys Val Leu Ser Asp Lys Ala
        430             435             440

Pro Cys Ile Thr Asp Trp Gln Gln Glu Asp Gly Thr Val His Arg Thr
    445             450             455

Tyr Leu Arg Gly Asn Leu Ala Glu Ser Lys Cys Tyr Leu Ile Thr Val
460             465             470

Thr Pro Val Tyr Ala Asp Gly Pro Gly Ser Pro Glu Ser Ile Lys Ala
475             480             485             490

Tyr Leu Lys Gln Ala Pro Pro Ser Lys Gly Pro Thr Val Arg Thr Lys
            495             500             505

Lys Val Gly Lys Asn Glu Ala Val Leu Glu Trp Asp Gln Leu Pro Val
        510             515             520

Asp Val Gln Asn Gly Phe Ile Arg Asn Tyr Thr Ile Phe Tyr Arg Thr
    525             530             535

Ile Ile Gly Asn Glu Thr Ala Val Asn Val Asp Ser Ser His Thr Glu
540             545             550

Tyr Thr Leu Ser Ser Leu Thr Ser Asp Thr Leu Tyr Met Val Arg Met
555             560             565             570

Ala Ala Tyr Thr Asp Glu Gly Gly Lys Asp Gly Pro Glu Phe Thr Phe
            575             580             585

Thr Thr Pro Lys Phe Ala Gln Gly Glu Ile Glu Ala Ile Val Val Pro
```

(2) INFORMATION FOR SEQ ID NO:3:

(i) SEQUENCE CHARACTERISTICS:
        (A) LENGTH: 705 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vii) IMMEDIATE SOURCE:
        (B) CLONE: hIgG1Fc (ix) FEATURE:
        (A) NAME/KEY: CDS
        (B) LOCATION: 1..699

(xi) SEQUENCE DESCRIPTION: SEQ ID NO:3:

```
                                                                                 590                                   595                                    600
Val Cys Leu Ala Phe Leu Leu Thr Thr Leu Leu Gly Val Leu Phe Cys
    605                       610                      615
Phe Asn Lys Arg Asp Leu Ile Lys Lys His Ile Trp Pro Asn Val Pro
620                           625                      630
Asp Pro Ser Lys Ser His Ile Ala Gln Trp Ser Pro His Thr Pro Pro
635                           640                      645                      650
Arg His Asn Phe Asn Ser Lys Asp Gln Met Tyr Ser Asp Gly Asn Phe
                          655                      660                      665
Thr Asp Val Ser Val Val Glu Ile Glu Ala Asn Asp Lys Lys Pro Phe
                670                       675                          680
Pro Glu Asp Leu
            685

GAG CCC AGA TCT TGT GAC AAA ACT CAC ACA TGC CCA CCG TGC CCA GCA        48
Glu Pro Arg Ser Cys Asp Lys Thr His Thr Cys Pro Pro Cys Pro Ala
  1               5                  10                  15

CCT GAA CTC CTG GGG GGA CCG TCA GTC TTC CTC TTC CCC CCA AAA CCC        96
Pro Glu Leu Leu Gly Gly Pro Ser Val Phe Leu Phe Pro Pro Lys Pro
                 20                  25                  30

AAG GAC ACC CTC ATG ATC TCC CGG ACC CCT GAG GTC ACA TGC GTG GTG       144
Lys Asp Thr Leu Met Ile Ser Arg Thr Pro Glu Val Thr Cys Val Val
             35                  40                  45

GTG GAC GTG AGC CAC GAA GAC CCT GAG GTC AAG TTC AAC TGG TAC GTG       192
Val Asp Val Ser His Glu Asp Pro Glu Val Lys Phe Asn Trp Tyr Val
 50                  55                  60

GAC GGC GTG GAG GTG CAT AAT GCC AAG ACA AAG CCG CGG GAG GAG CAG       240
Asp Gly Val Glu Val His Asn Ala Lys Thr Lys Pro Arg Glu Glu Gln
 65                  70                  75                  80

TAC AAC AGC ACG TAC CGG GTG GTC AGC GTC CTC ACC GTC CTG CAC CAG       288
Tyr Asn Ser Thr Tyr Arg Val Val Ser Val Leu Thr Val Leu His Gln
             85                  90                  95

GAC TGG CTG AAT GGC AAG GAC TAC AAG TGC AAG GTC TCC AAC AAA GCC       336
Asp Trp Leu Asn Gly Lys Asp Tyr Lys Cys Lys Val Ser Asn Lys Ala
                100                 105                 110

CTC CCA GCC CCC ATG CAG AAA ACC ATC TCC AAA GCC AAA GGG CAG CCC       384
Leu Pro Ala Pro Met Gln Lys Thr Ile Ser Lys Ala Lys Gly Gln Pro
        115                 120                 125

CGA GAA CCA CAG GTG TAC ACC CTG CCC CCA TCC CGG GAT GAG CTG ACC       432
Arg Glu Pro Gln Val Tyr Thr Leu Pro Pro Ser Arg Asp Glu Leu Thr
130                 135                 140

AAG AAC CAG GTC AGC CTG ACC TGC CTG GTC AAA GGC TTC TAT CCC AGG       480
Lys Asn Gln Val Ser Leu Thr Cys Leu Val Lys Gly Phe Tyr Pro Arg
```

```
145                      150                      155                      160
CAC ATC GCC GTG GAG TGG GAG AGC AAT GGG CAG CCG GAG AAC AAC TAC           528
His Ile Ala Val Glu Trp Glu Ser Asn Gly Gln Pro Glu Asn Asn Tyr
                    165                     170                 175

AAG ACC ACG CCT CCC GTG CTG GAC TCC GAC GGC TCC TTC TTC CTC TAC           576
Lys Thr Thr Pro Pro Val Leu Asp Ser Asp Gly Ser Phe Phe Leu Tyr
                180                     185                     190

AGC AAG CTC ACC GTG GAC AAG AGC AGG TGG CAG CAG GGG AAC GTC TTC           624
Ser Lys Leu Thr Val Asp Lys Ser Arg Trp Gln Gln Gly Asn Val Phe
            195                     200                     205

TCA TGC TCC GTG ATG CAT GAG GCT CTG CAC AAC CAC TAC ACG CAG AAG           672
Ser Cys Ser Val Met His Glu Ala Leu His Asn His Tyr Thr Gln Lys
        210                     215                     220

AGC CTC TCC CTG TCT CCG GGT AAA TGAACTAGT                                 705
Ser Leu Ser Leu Ser Pro Gly Lys
225                 230
```

( 2 ) INFORMATION FOR SEQ ID NO:4:

( i ) SEQUENCE CHARACTERISTICS:
        ( A ) LENGTH: 232 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Glu Pro Arg Ser Cys Asp Lys Thr His Thr Cys Pro Pro Cys Pro Ala
 1               5                  10                      15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                      45

Val Asp Val Ser His Glu Asp Pro Glu Val Lys Phe Asn Trp Tyr Val
        50                  55                      60

Asp Gly Val Glu Val His Asn Ala Lys Thr Lys Pro Arg Glu Glu Gln
65                  70                  75                      80

Tyr Asn Ser Thr Tyr Arg Val Val Ser Val Leu Thr Val Leu His Gln
                85                  90                      95

Asp Trp Leu Asn Gly Lys Asp Tyr Lys Cys Lys Val Ser Asn Lys Ala
                100                 105                 110

Leu Pro Ala Pro Met Gln Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Arg
145                 150                 155                 160

His Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly Lys
225                 230
```

( 2 ) INFORMATION FOR SEQ ID NO:5:

( i ) SEQUENCE CHARACTERISTICS:
  ( A ) LENGTH: 3182 base pairs
  ( B ) TYPE: nucleic acid
  ( C ) STRANDEDNESS: single
  ( D ) TOPOLOGY: linear ( i i ) MOLECULE TYPE: cDNA to mRNA ( i i i ) HYPOTHETICAL: NO ( i v ) ANTI-SENSE: NO ( v ) FRAGMENT TYPE: N-terminal ( v i ) ORIGINAL SOURCE:
  ( F ) TISSUE TYPE: human placenta ( v i i ) IMMEDIATE SOURCE:
  ( B ) CLONE: pHLIFR-65

( i x ) FEATURE:
  ( A ) NAME/KEY: matpeptide
  ( B ) LOCATION: 311..3182

( i x ) FEATURE:
  ( A ) NAME/KEY: CDS
  ( B ) LOCATION: 179..3182

( i x ) FEATURE:
  ( A ) NAME/KEY: sigpeptide
  ( B ) LOCATION: 179..310

( i x ) FEATURE:
  ( A ) NAME/KEY: matpeptide
  ( B ) LOCATION: 311..3182

( x i ) SEQUENCE DESCRIPTION: SEQ ID NO:5:

```
AGATCTTGGA ACGAGACGAC CTGCTCTCTC TCCCAGAACG TGTCTCTGCT GCAAGGCACC      60

GGGCCCTTTC GCTCTGCAGA ACTGCACTTG CAAGACCATT ATCAACTCCT AATCCCAGCT     120

CAGAAAGGGA GCCTCTGCGA CTCATTCATC GCCCTCCAGG ACTGACTGCA TTGCACAG       178

ATG ATG GAT ATT TAC GTA TGT TTG AAA CGA CCA TCC TGG ATG GTG GAC       226
Met Met Asp Ile Tyr Val Cys Leu Lys Arg Pro Ser Trp Met Val Asp
-44          -40                 -35                 -30

AAT AAA AGA ATG AGG ACT GCT TCA AAT TTC CAG TGG CTG TTA TCA ACA       274
Asn Lys Arg Met Arg Thr Ala Ser Asn Phe Gln Trp Leu Leu Ser Thr
            -25                 -20                 -15

TTT ATT CTT CTA TAT CTA ATG AAT CAA GTA AAT AGC CAG AAA AAG GGG       322
Phe Ile Leu Leu Tyr Leu Met Asn Gln Val Asn Ser Gln Lys Lys Gly
        -10                  -5                  1

GCT CCT CAT GAT TTG AAG TGT GTA ACT AAC AAT TTG CAA GTG TGG AAC       370
Ala Pro His Asp Leu Lys Cys Val Thr Asn Asn Leu Gln Val Trp Asn
 5                10                  15                  20

TGT TCT TGG AAA GCA CCC TCT GGA ACA GGC CGT GGT ACT GAT TAT GAA       418
Cys Ser Trp Lys Ala Pro Ser Gly Thr Gly Arg Gly Thr Asp Tyr Glu
             25                  30                  35

GTT TGC ATT GAA AAC AGG TCC CGT TCT TGT TAT CAG TTG GAG AAA ACC       466
Val Cys Ile Glu Asn Arg Ser Arg Ser Cys Tyr Gln Leu Glu Lys Thr
         40                  45                  50

AGT ATT AAA ATT CCA GCT CTT TCA CAT GGT GAT TAT GAA ATA ACA ATA       514
Ser Ile Lys Ile Pro Ala Leu Ser His Gly Asp Tyr Glu Ile Thr Ile
         55                  60                  65

AAT TCT CTA CAT GAT TTT GGA AGT TCT ACA AGT AAA TTC ACA CTA AAT       562
Asn Ser Leu His Asp Phe Gly Ser Ser Thr Ser Lys Phe Thr Leu Asn
 70                  75                  80

GAA CAA AAC GTT TCC TTA ATT CCA GAT ACT CCA GAG ATC TTG AAT TTG       610
Glu Gln Asn Val Ser Leu Ile Pro Asp Thr Pro Glu Ile Leu Asn Leu
 85                  90                  95                 100

TCT GCT GAT TTC TCA ACC TCT ACA TTA TAC CTA AAG TGG AAC GAC AGG       658
Ser Ala Asp Phe Ser Thr Ser Thr Leu Tyr Leu Lys Trp Asn Asp Arg
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     |     |     | 105 |     |     |     |     | 110 |     |     |     |     | 115 |     |     |
| GGT | TCA | GTT | TTT | CCA | CAC | CGC | TCA | AAT | GTT | ATC | TGG | GAA | ATT | AAA | GTT | 706 |
| Gly | Ser | Val<br>120 | Phe | Pro | His | Arg | Ser | Asn<br>125 | Val | Ile | Trp | Glu | Ile<br>130 | Lys | Val |     |
| CTA | CGT | AAA | GAG | AGT | ATG | GAG | CTC | GTA | AAA | TTA | GTG | ACC | CAC | AAC | ACA | 754 |
| Leu | Arg | Lys<br>135 | Glu | Ser | Met | Glu | Leu<br>140 | Val | Lys | Leu | Val | Thr<br>145 | His | Asn | Thr |     |
| ACT | CTG | AAT | GGC | AAA | GAT | ACA | CTT | CAT | CAC | TGG | AGT | TGG | GCC | TCA | GAT | 802 |
| Thr | Leu<br>150 | Asn | Gly | Lys | Asp | Thr | Leu<br>155 | His | His | Trp | Ser | Trp<br>160 | Ala | Ser | Asp |     |
| ATG | CCC | TTG | GAA | TGT | GCC | ATT | CAT | TTT | GTG | GAA | ATT | AGA | TGC | TAC | ATT | 850 |
| Met<br>165 | Pro | Leu | Glu | Cys | Ala<br>170 | Ile | His | Phe | Val | Glu<br>175 | Ile | Arg | Cys | Tyr | Ile<br>180 |     |
| GAC | AAT | CTT | CAT | TTT | TCT | GGT | CTC | GAA | GAG | TGG | AGT | GAC | TGG | AGC | CCT | 898 |
| Asp | Asn | Leu | His | Phe<br>185 | Ser | Gly | Leu | Glu | Glu<br>190 | Trp | Ser | Asp | Trp | Ser<br>195 | Pro |     |
| GTG | AAG | AAC | ATT | TCT | TGG | ATA | CCT | GAT | TCT | CAG | ACT | AAG | GTT | TTT | CCT | 946 |
| Val | Lys | Asn | Ile | Ser<br>200 | Trp | Ile | Pro | Asp | Ser<br>205 | Gln | Thr | Lys | Val | Phe<br>210 | Pro |     |
| CAA | GAT | AAA | GTG | ATA | CTT | GTA | GGC | TCA | GAC | ATA | ACA | TTT | TGT | TGT | GTG | 994 |
| Gln | Asp | Lys<br>215 | Val | Ile | Leu | Val | Gly<br>220 | Ser | Asp | Ile | Thr | Phe<br>225 | Cys | Cys | Val |     |
| AGT | CAA | GAA | AAA | GTG | TTA | TCA | GCA | CTG | ATT | GGC | CAT | ACA | AAC | TGC | CCC | 1042 |
| Ser | Gln | Glu<br>230 | Lys | Val | Leu | Ser | Ala<br>235 | Leu | Ile | Gly | His | Thr<br>240 | Asn | Cys | Pro |     |
| TTG | ATC | CAT | CTT | GAT | GGG | GAA | AAT | GTT | GCA | ATC | AAG | ATT | CGT | AAT | ATT | 1090 |
| Leu<br>245 | Ile | His | Leu | Asp | Gly<br>250 | Glu | Asn | Val | Ala | Ile<br>255 | Lys | Ile | Arg | Asn | Ile<br>260 |     |
| TCT | GTT | TCT | GCA | AGT | AGT | GGA | ACA | AAT | GTA | GTT | TTT | ACA | ACC | GAA | GAT | 1138 |
| Ser | Val | Ser | Ala | Ser<br>265 | Ser | Gly | Thr | Asn | Val<br>270 | Val | Phe | Thr | Thr | Glu<br>275 | Asp |     |
| AAC | ATA | TTT | GGA | ACC | GTT | ATT | TTT | GCT | GGA | TAT | CCA | CCA | GAT | ACT | CCT | 1186 |
| Asn | Ile | Phe | Gly | Thr<br>280 | Val | Ile | Phe | Ala | Gly<br>285 | Tyr | Pro | Pro | Asp | Thr<br>290 | Pro |     |
| CAA | CAA | CTG | AAT | TGT | GAG | ACA | CAT | GAT | TTA | AAA | GAA | ATT | ATA | TGT | AGT | 1234 |
| Gln | Gln | Leu | Asn<br>295 | Cys | Glu | Thr | His | Asp<br>300 | Leu | Lys | Glu | Ile | Ile<br>305 | Cys | Ser |     |
| TGG | AAT | CCA | GGA | AGG | GTG | ACA | GCG | TTG | GTG | GGC | CCA | CGT | GCT | ACA | AGC | 1282 |
| Trp | Asn | Pro<br>310 | Gly | Arg | Val | Thr | Ala<br>315 | Leu | Val | Gly | Pro | Arg<br>320 | Ala | Thr | Ser |     |
| TAC | ACT | TTA | GTT | GAA | AGT | TTT | TCA | GGA | AAA | TAT | GTT | AGA | CTT | AAA | AGA | 1330 |
| Tyr | Thr | Leu<br>325 | Val | Glu | Ser | Phe | Ser<br>330 | Gly | Lys | Tyr | Val | Arg<br>335 | Leu | Lys | Arg<br>340 |     |
| GCT | GAA | GCA | CCT | ACA | AAC | GAA | AGC | TAT | CAA | TTA | TTA | TTT | CAA | ATG | CTT | 1378 |
| Ala | Glu | Ala | Pro | Thr<br>345 | Asn | Glu | Ser | Tyr | Gln<br>350 | Leu | Leu | Phe | Gln | Met<br>355 | Leu |     |
| CCA | AAT | CAA | GAA | ATA | TAT | AAT | TTT | ACT | TTG | AAT | GCT | CAC | AAT | CCG | CTG | 1426 |
| Pro | Asn | Gln | Glu | Ile<br>360 | Tyr | Asn | Phe | Thr | Leu<br>365 | Asn | Ala | His | Asn | Pro<br>370 | Leu |     |
| GGT | CGA | TCA | CAA | TCA | ACA | ATT | TTA | GTT | AAT | ATA | ACT | GAA | AAA | GTT | TAT | 1474 |
| Gly | Arg | Ser | Gln | Ser<br>375 | Thr | Ile | Leu | Val | Asn<br>380 | Ile | Thr | Glu | Lys | Val<br>385 | Tyr |     |
| CCC | CAT | ACT | CCT | ACT | TCA | TTC | AAA | GTG | AAG | GAT | ATT | AAT | TCA | ACA | GCT | 1522 |
| Pro | His | Thr | Pro<br>390 | Thr | Ser | Phe | Lys | Val<br>395 | Lys | Asp | Ile | Asn | Ser<br>400 | Thr | Ala |     |
| GTT | AAA | CTT | TCT | TGG | CAT | TTA | CCA | GGC | AAC | TTT | GCA | AAG | ATT | AAT | TTT | 1570 |
| Val | Lys | Leu | Ser<br>405 | Trp | His | Leu | Pro | Gly<br>410 | Asn | Phe | Ala | Lys | Ile<br>415 | Asn | Phe<br>420 |     |
| TTA | TGT | GAA | ATT | GAA | ATT | AAG | AAA | TCT | AAT | TCA | GTA | CAA | GAG | CAG | CGG | 1618 |
| Leu | Cys | Glu | Ile | Glu<br>425 | Ile | Lys | Lys | Ser | Asn<br>430 | Ser | Val | Gln | Glu | Gln<br>435 | Arg |     |

| | | | | | | | | | | | | | | | | |
|---|---|---|---|---|---|---|---|---|---|---|---|---|---|---|---|---|
| AAT | GTC | ACA | ATC | AAA | GGA | GTA | GAA | AAT | TCA | AGT | TAT | CTT | GTT | GCT | CTG | 1666 |
| Asn | Val | Thr | Ile | Lys | Gly | Val | Glu | Asn | Ser | Ser | Tyr | Leu | Val | Ala | Leu | |
| | | | 440 | | | | | 445 | | | | | 450 | | | |
| GAC | AAG | TTA | AAT | CCA | TAC | ACT | CTA | TAT | ACT | TTT | CGG | ATT | CGT | TGT | TCT | 1714 |
| Asp | Lys | Leu | Asn | Pro | Tyr | Thr | Leu | Tyr | Thr | Phe | Arg | Ile | Arg | Cys | Ser | |
| | | 455 | | | | | 460 | | | | | 465 | | | | |
| ACT | GAA | ACT | TTC | TGG | AAA | TGG | AGC | AAA | TGG | AGC | AAT | AAA | AAA | CAA | CAT | 1762 |
| Thr | Glu | Thr | Phe | Trp | Lys | Trp | Ser | Lys | Trp | Ser | Asn | Lys | Lys | Gln | His | |
| | 470 | | | | | 475 | | | | | 480 | | | | | |
| TTA | ACA | ACA | GAA | GCC | AGT | CCT | TCA | AAG | GGG | CCT | GAT | ACT | TGG | AGA | GAG | 1810 |
| Leu | Thr | Thr | Glu | Ala | Ser | Pro | Ser | Lys | Gly | Pro | Asp | Thr | Trp | Arg | Glu | |
| 485 | | | | | 490 | | | | | 495 | | | | | 500 | |
| TGG | AGT | TCT | GAT | GGA | AAA | AAT | TTA | ATA | ATC | TAT | TGG | AAG | CCT | TTA | CCC | 1858 |
| Trp | Ser | Ser | Asp | Gly | Lys | Asn | Leu | Ile | Ile | Tyr | Trp | Lys | Pro | Leu | Pro | |
| | | | | 505 | | | | | 510 | | | | | 515 | | |
| ATT | AAT | GAA | GCT | AAT | GGA | AAA | ATA | CTT | TCC | TAC | AAT | GTA | TCG | TGT | TCA | 1906 |
| Ile | Asn | Glu | Ala | Asn | Gly | Lys | Ile | Leu | Ser | Tyr | Asn | Val | Ser | Cys | Ser | |
| | | | 520 | | | | | 525 | | | | | 530 | | | |
| TCA | GAT | GAG | GAA | ACA | CAG | TCC | CTT | TCT | GAA | ATC | CCT | GAT | CCT | CAG | CAC | 1954 |
| Ser | Asp | Glu | Glu | Thr | Gln | Ser | Leu | Ser | Glu | Ile | Pro | Asp | Pro | Gln | His | |
| | | 535 | | | | | 540 | | | | | 545 | | | | |
| AAA | GCA | GAG | ATA | CGA | CTT | GAT | AAG | AAT | GAC | TAC | ATC | ATC | AGC | GTA | GTG | 2002 |
| Lys | Ala | Glu | Ile | Arg | Leu | Asp | Lys | Asn | Asp | Tyr | Ile | Ile | Ser | Val | Val | |
| | 550 | | | | | 555 | | | | | 560 | | | | | |
| GCT | AAA | AAT | TCT | GTG | GGC | TCA | TCA | CCA | CCT | TCC | AAA | ATA | GCG | AGT | ATG | 2050 |
| Ala | Lys | Asn | Ser | Val | Gly | Ser | Ser | Pro | Pro | Ser | Lys | Ile | Ala | Ser | Met | |
| 565 | | | | | 570 | | | | | 575 | | | | | 580 | |
| GAA | ATT | CCA | AAT | GAT | GAT | CTC | AAA | ATA | GAA | CAA | GTT | GTT | GGG | ATG | GGA | 2098 |
| Glu | Ile | Pro | Asn | Asp | Asp | Leu | Lys | Ile | Glu | Gln | Val | Val | Gly | Met | Gly | |
| | | | | 585 | | | | | 590 | | | | | 595 | | |
| AAG | GGG | ATT | CTC | CTC | ACC | TGG | CAT | TAC | GAC | CCC | AAC | ATG | ACT | TGC | GAC | 2146 |
| Lys | Gly | Ile | Leu | Leu | Thr | Trp | His | Tyr | Asp | Pro | Asn | Met | Thr | Cys | Asp | |
| | | | 600 | | | | | 605 | | | | | 610 | | | |
| TAC | GTC | ATT | AAG | TGG | TGT | AAC | TCG | TCT | CGG | TCG | GAA | CCA | TGC | CTT | ATG | 2194 |
| Tyr | Val | Ile | Lys | Trp | Cys | Asn | Ser | Ser | Arg | Ser | Glu | Pro | Cys | Leu | Met | |
| | | 615 | | | | | 620 | | | | | 625 | | | | |
| GAC | TGG | AGA | AAA | GTT | CCC | TCA | AAC | AGC | ACT | GAA | ACT | GTA | ATA | GAA | TCT | 2242 |
| Asp | Trp | Arg | Lys | Val | Pro | Ser | Asn | Ser | Thr | Glu | Thr | Val | Ile | Glu | Ser | |
| | 630 | | | | | 635 | | | | | 640 | | | | | |
| GAT | GAG | TTT | CGA | CCA | GGT | ATA | AGA | TAT | AAT | TTT | TTC | CTG | TAT | GGA | TGC | 2290 |
| Asp | Glu | Phe | Arg | Pro | Gly | Ile | Arg | Tyr | Asn | Phe | Phe | Leu | Tyr | Gly | Cys | |
| 645 | | | | | 650 | | | | | 655 | | | | | 660 | |
| AGA | AAT | CAA | GGA | TAT | CAA | TTA | TTA | CGC | TCC | ATG | ATT | GGA | TAT | ATA | GAA | 2338 |
| Arg | Asn | Gln | Gly | Tyr | Gln | Leu | Leu | Arg | Ser | Met | Ile | Gly | Tyr | Ile | Glu | |
| | | | | 665 | | | | | 670 | | | | | 675 | | |
| GAA | TTG | GCT | CCC | ATT | GTT | GCA | CCA | AAT | TTT | ACT | GTT | GAG | GAT | ACT | TCT | 2386 |
| Glu | Leu | Ala | Pro | Ile | Val | Ala | Pro | Asn | Phe | Thr | Val | Glu | Asp | Thr | Ser | |
| | | | 680 | | | | | 685 | | | | | 690 | | | |
| GCA | GAT | TCG | ATA | TTA | GTA | AAA | TGG | GAA | GAC | ATT | CCT | GTG | GAA | GAA | CTT | 2434 |
| Ala | Asp | Ser | Ile | Leu | Val | Lys | Trp | Glu | Asp | Ile | Pro | Val | Glu | Glu | Leu | |
| | | 695 | | | | | 700 | | | | | 705 | | | | |
| AGA | GGC | TTT | TTA | AGA | GGA | TAT | TTG | TTT | TAC | TTT | GGA | AAA | GGA | GAA | AGA | 2482 |
| Arg | Gly | Phe | Leu | Arg | Gly | Tyr | Leu | Phe | Tyr | Phe | Gly | Lys | Gly | Glu | Arg | |
| | 710 | | | | | 715 | | | | | 720 | | | | | |
| GAC | ACA | TCT | AAG | ATG | AGG | GTT | TTA | GAA | TCA | GGT | CGT | TCT | GAC | ATA | AAA | 2530 |
| Asp | Thr | Ser | Lys | Met | Arg | Val | Leu | Glu | Ser | Gly | Arg | Ser | Asp | Ile | Lys | |
| 725 | | | | | 730 | | | | | 735 | | | | | 740 | |
| GTT | AAG | AAT | ATT | ACT | GAC | ATA | TCC | CAG | AAG | ACA | CTG | AGA | ATT | GCT | GAT | 2578 |
| Val | Lys | Asn | Ile | Thr | Asp | Ile | Ser | Gln | Lys | Thr | Leu | Arg | Ile | Ala | Asp | |
| | | | | 745 | | | | | 750 | | | | | 755 | | |
| CTT | CAA | GGT | AAA | ACA | AGT | TAC | CAC | CTG | GTC | TTG | CGA | GCC | TAT | ACA | GAT | 2626 |
| Leu | Gln | Gly | Lys | Thr | Ser | Tyr | His | Leu | Val | Leu | Arg | Ala | Tyr | Thr | Asp | |

-continued

```
                              760                      765                          770
GGT  GGA  GTG  GGC  CCG  GAG  AAG  AGT  ATG  TAT  GTG  GTG  ACA  AAG  GAA  AAT              2674
Gly  Gly  Val  Gly  Pro  Glu  Lys  Ser  Met  Tyr  Val  Val  Thr  Lys  Glu  Asn
          775                      780                     785

TCT  GTG  GGA  TTA  ATT  ATT  GCC  ATT  CTC  ATC  CCA  GTG  GCA  GTG  GCT  GTC              2722
Ser  Val  Gly  Leu  Ile  Ile  Ala  Ile  Leu  Ile  Pro  Val  Ala  Val  Ala  Val
          790                      795                     800

ATT  GTT  GGA  GTG  GTG  ACA  AGT  ATC  CTT  TGC  TAT  CGG  AAA  CGA  GAA  TGG              2770
Ile  Val  Gly  Val  Val  Thr  Ser  Ile  Leu  Cys  Tyr  Arg  Lys  Arg  Glu  Trp
805                      810                     815                          820

ATT  AAA  GAA  ACC  TTC  TAC  CCT  GAT  ATT  CCA  AAT  CCA  GAA  AAC  TGT  AAA              2818
Ile  Lys  Glu  Thr  Phe  Tyr  Pro  Asp  Ile  Pro  Asn  Pro  Glu  Asn  Cys  Lys
                         825                     830                          835

GCA  TTA  CAG  TTT  CAA  AAG  AGT  GTC  TGT  GAG  GGA  AGC  AGT  GCT  CTT  AAA              2866
Ala  Leu  Gln  Phe  Gln  Lys  Ser  Val  Cys  Glu  Gly  Ser  Ser  Ala  Leu  Lys
               840                      845                     850

ACA  TTG  GAA  ATG  AAT  CCT  TGT  ACC  CCA  AAT  AAT  GTT  GAG  GTT  CTG  GAA              2914
Thr  Leu  Glu  Met  Asn  Pro  Cys  Thr  Pro  Asn  Asn  Val  Glu  Val  Leu  Glu
          855                      860                     865

ACT  CGA  TCA  GCA  TTT  CCT  AAA  ATA  GAA  GAT  ACA  GAA  ATA  ATT  TCC  CCA              2962
Thr  Arg  Ser  Ala  Phe  Pro  Lys  Ile  Glu  Asp  Thr  Glu  Ile  Ile  Ser  Pro
     870                      875                     880

GTA  GCT  GAG  CGT  CCT  GAA  GAT  CGC  TCT  GAT  GCA  GAG  CCT  GAA  AAC  CAT              3010
Val  Ala  Glu  Arg  Pro  Glu  Asp  Arg  Ser  Asp  Ala  Glu  Pro  Glu  Asn  His
885                      890                     895                          900

GTG  GTT  GTG  TCC  TAT  TGT  CCA  CCC  ATC  ATT  GAG  GAA  GAA  ATA  CCA  AAC              3058
Val  Val  Val  Ser  Tyr  Cys  Pro  Pro  Ile  Ile  Glu  Glu  Glu  Ile  Pro  Asn
                    905                      910                     915

CCA  GCC  GCA  GAT  GAA  GCT  GGA  GGG  ACT  GCA  CAG  GTT  ATT  TAC  ATT  GAT              3106
Pro  Ala  Ala  Asp  Glu  Ala  Gly  Gly  Thr  Ala  Gln  Val  Ile  Tyr  Ile  Asp
               920                      925                     930

GTT  CAG  TCG  ATG  TAT  CAG  CCT  CAA  GCA  AAA  CCA  GAA  GAA  AAA  AAA  AAA              3154
Val  Gln  Ser  Met  Tyr  Gln  Pro  Gln  Ala  Lys  Pro  Glu  Glu  Lys  Lys  Lys
          935                      940                     945

AAA  AGC  AGG  TCG  TCT  CGT  TCC  AAG  ATC  T                                               3182
Lys  Ser  Arg  Ser  Ser  Arg  Ser  Lys  Ile
     950                      955
```

( 2 ) INFORMATION FOR SEQ ID NO:6:

( i ) SEQUENCE CHARACTERISTICS:
        ( A ) LENGTH: 1001 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Met  Asp  Ile  Tyr  Val  Cys  Leu  Lys  Arg  Pro  Ser  Trp  Met  Val  Asp
-44            -40                      -35                      -30

Asn  Lys  Arg  Met  Arg  Thr  Ala  Ser  Asn  Phe  Gln  Trp  Leu  Leu  Ser  Thr
          -25                      -20                           -15

Phe  Ile  Leu  Leu  Tyr  Leu  Met  Asn  Gln  Val  Asn  Ser  Gln  Lys  Lys  Gly
          -10                       -5                             1

Ala  Pro  His  Asp  Leu  Lys  Cys  Val  Thr  Asn  Leu  Gln  Val  Trp  Asn
  5                     10                      15                      20

Cys  Ser  Trp  Lys  Ala  Pro  Ser  Gly  Thr  Gly  Arg  Gly  Thr  Asp  Tyr  Glu
               25                      30                      35

Val  Cys  Ile  Glu  Asn  Arg  Ser  Arg  Ser  Cys  Tyr  Gln  Leu  Glu  Lys  Thr
               40                      45                      50

Ser  Ile  Lys  Ile  Pro  Ala  Leu  Ser  His  Gly  Asp  Tyr  Glu  Ile  Thr  Ile
          55                      60                      65
```

```
Asn Ser Leu His Asp Phe Gly Ser Ser Thr Ser Lys Phe Thr Leu Asn
    70              75              80
Glu Gln Asn Val Ser Leu Ile Pro Asp Thr Pro Glu Ile Leu Asn Leu
85              90              95                          100
Ser Ala Asp Phe Ser Thr Ser Thr Leu Tyr Leu Lys Trp Asn Asp Arg
                105             110             115
Gly Ser Val Phe Pro His Arg Ser Asn Val Ile Trp Glu Ile Lys Val
            120             125             130
Leu Arg Lys Glu Ser Met Glu Leu Val Lys Leu Val Thr His Asn Thr
        135             140             145
Thr Leu Asn Gly Lys Asp Thr Leu His His Trp Ser Trp Ala Ser Asp
    150             155             160
Met Pro Leu Glu Cys Ala Ile His Phe Val Glu Ile Arg Cys Tyr Ile
165             170             175                         180
Asp Asn Leu His Phe Ser Gly Leu Glu Glu Trp Ser Asp Trp Ser Pro
                185             190             195
Val Lys Asn Ile Ser Trp Ile Pro Asp Ser Gln Thr Lys Val Phe Pro
            200             205             210
Gln Asp Lys Val Ile Leu Val Gly Ser Asp Ile Thr Phe Cys Cys Val
        215             220             225
Ser Gln Glu Lys Val Leu Ser Ala Leu Ile Gly His Thr Asn Cys Pro
    230             235             240
Leu Ile His Leu Asp Gly Glu Asn Val Ala Ile Lys Ile Arg Asn Ile
245             250             255                         260
Ser Val Ser Ala Ser Ser Gly Thr Asn Val Val Phe Thr Thr Glu Asp
                265             270             275
Asn Ile Phe Gly Thr Val Ile Phe Ala Gly Tyr Pro Pro Asp Thr Pro
            280             285             290
Gln Gln Leu Asn Cys Glu Thr His Asp Leu Lys Glu Ile Ile Cys Ser
        295             300             305
Trp Asn Pro Gly Arg Val Thr Ala Leu Val Gly Pro Arg Ala Thr Ser
    310             315             320
Tyr Thr Leu Val Glu Ser Phe Ser Gly Lys Tyr Val Arg Leu Lys Arg
325             330             335                         340
Ala Glu Ala Pro Thr Asn Glu Ser Tyr Gln Leu Leu Phe Gln Met Leu
                345             350             355
Pro Asn Gln Glu Ile Tyr Asn Phe Thr Leu Asn Ala His Asn Pro Leu
            360             365             370
Gly Arg Ser Gln Ser Thr Ile Leu Val Asn Ile Thr Glu Lys Val Tyr
        375             380             385
Pro His Thr Pro Thr Ser Phe Lys Val Lys Asp Ile Asn Ser Thr Ala
    390             395             400
Val Lys Leu Ser Trp His Leu Pro Gly Asn Phe Ala Lys Ile Asn Phe
405             410             415                         420
Leu Cys Glu Ile Glu Ile Lys Lys Ser Asn Ser Val Gln Glu Gln Arg
                425             430             435
Asn Val Thr Ile Lys Gly Val Glu Asn Ser Ser Tyr Leu Val Ala Leu
            440             445             450
Asp Lys Leu Asn Pro Tyr Thr Leu Tyr Thr Phe Arg Ile Arg Cys Ser
        455             460             465
Thr Glu Thr Phe Trp Lys Trp Ser Lys Trp Ser Asn Lys Lys Gln His
    470             475             480
Leu Thr Thr Glu Ala Ser Pro Ser Lys Gly Pro Asp Thr Trp Arg Glu
485             490             495                         500
```

-continued

| | | | | | | | | | | | | | |
|---|---|---|---|---|---|---|---|---|---|---|---|---|---|
| Trp | Ser | Ser | Asp | Gly | Lys | Asn | Leu | Ile | Ile | Tyr | Trp | Lys | Pro | Leu | Pro |
| | | | | 505 | | | | 510 | | | | | 515 | | |
| Ile | Asn | Glu | Ala | Asn | Gly | Lys | Ile | Leu | Ser | Tyr | Asn | Val | Ser | Cys | Ser |
| | | | 520 | | | | | 525 | | | | 530 | | | |
| Ser | Asp | Glu | Glu | Thr | Gln | Ser | Leu | Ser | Glu | Ile | Pro | Asp | Pro | Gln | His |
| | | | 535 | | | | | 540 | | | | 545 | | | |
| Lys | Ala | Glu | Ile | Arg | Leu | Asp | Lys | Asn | Asp | Tyr | Ile | Ile | Ser | Val | Val |
| | 550 | | | | | | 555 | | | | 560 | | | | |
| Ala | Lys | Asn | Ser | Val | Gly | Ser | Ser | Pro | Ser | Lys | Ile | Ala | Ser | Met |
| 565 | | | | | 570 | | | | 575 | | | | | 580 |
| Glu | Ile | Pro | Asn | Asp | Asp | Leu | Lys | Ile | Glu | Gln | Val | Val | Gly | Met | Gly |
| | | | | 585 | | | | 590 | | | | | 595 | | |
| Lys | Gly | Ile | Leu | Leu | Thr | Trp | His | Tyr | Asp | Pro | Asn | Met | Thr | Cys | Asp |
| | | | 600 | | | | 605 | | | | | 610 | | | |
| Tyr | Val | Ile | Lys | Trp | Cys | Asn | Ser | Ser | Arg | Ser | Glu | Pro | Cys | Leu | Met |
| | | 615 | | | | 620 | | | | | 625 | | | | |
| Asp | Trp | Arg | Lys | Val | Pro | Ser | Asn | Ser | Thr | Glu | Thr | Val | Ile | Glu | Ser |
| | 630 | | | | | 635 | | | | 640 | | | | | |
| Asp | Glu | Phe | Arg | Pro | Gly | Ile | Arg | Tyr | Asn | Phe | Phe | Leu | Tyr | Gly | Cys |
| 645 | | | | | 650 | | | | 655 | | | | | 660 | |
| Arg | Asn | Gln | Gly | Tyr | Gln | Leu | Leu | Arg | Ser | Met | Ile | Gly | Tyr | Ile | Glu |
| | | | | 665 | | | | 670 | | | | | 675 | | |
| Glu | Leu | Ala | Pro | Ile | Val | Ala | Pro | Asn | Phe | Thr | Val | Glu | Asp | Thr | Ser |
| | | | 680 | | | | 685 | | | | | 690 | | | |
| Ala | Asp | Ser | Ile | Leu | Val | Lys | Trp | Glu | Asp | Ile | Pro | Val | Glu | Glu | Leu |
| | | 695 | | | | 700 | | | | | 705 | | | | |
| Arg | Gly | Phe | Leu | Arg | Gly | Tyr | Leu | Phe | Tyr | Phe | Gly | Lys | Gly | Glu | Arg |
| | 710 | | | | | 715 | | | | 720 | | | | | |
| Asp | Thr | Ser | Lys | Met | Arg | Val | Leu | Glu | Ser | Gly | Arg | Ser | Asp | Ile | Lys |
| 725 | | | | 730 | | | | 735 | | | | | 740 | | |
| Val | Lys | Asn | Ile | Thr | Asp | Ile | Ser | Gln | Lys | Thr | Leu | Arg | Ile | Ala | Asp |
| | | | | 745 | | | | 750 | | | | | 755 | | |
| Leu | Gln | Gly | Lys | Thr | Ser | Tyr | His | Leu | Val | Leu | Arg | Ala | Tyr | Thr | Asp |
| | | | 760 | | | | 765 | | | | | 770 | | | |
| Gly | Gly | Val | Gly | Pro | Glu | Lys | Ser | Met | Tyr | Val | Val | Thr | Lys | Glu | Asn |
| | | 775 | | | | 780 | | | | | 785 | | | | |
| Ser | Val | Gly | Leu | Ile | Ile | Ala | Ile | Leu | Ile | Pro | Val | Ala | Val | Ala | Val |
| | 790 | | | | 795 | | | | | 800 | | | | | |
| Ile | Val | Gly | Val | Val | Thr | Ser | Ile | Leu | Cys | Tyr | Arg | Lys | Arg | Glu | Trp |
| 805 | | | | | 810 | | | | 815 | | | | | 820 | |
| Ile | Lys | Glu | Thr | Phe | Tyr | Pro | Asp | Ile | Pro | Asn | Pro | Glu | Asn | Cys | Lys |
| | | | | 825 | | | | 830 | | | | | 835 | | |
| Ala | Leu | Gln | Phe | Gln | Lys | Ser | Val | Cys | Glu | Gly | Ser | Ser | Ala | Leu | Lys |
| | | | 840 | | | | 845 | | | | | 850 | | | |
| Thr | Leu | Glu | Met | Asn | Pro | Cys | Thr | Pro | Asn | Asn | Val | Glu | Val | Leu | Glu |
| | | 855 | | | | 860 | | | | | 865 | | | | |
| Thr | Arg | Ser | Ala | Phe | Pro | Lys | Ile | Glu | Asp | Thr | Glu | Ile | Ile | Ser | Pro |
| 870 | | | | | 875 | | | | 880 | | | | | | |
| Val | Ala | Glu | Arg | Pro | Glu | Asp | Arg | Ser | Asp | Ala | Glu | Pro | Glu | Asn | His |
| 885 | | | | | 890 | | | | 895 | | | | | 900 | |
| Val | Val | Val | Ser | Tyr | Cys | Pro | Pro | Ile | Ile | Glu | Glu | Glu | Ile | Pro | Asn |
| | | | | 905 | | | | 910 | | | | | 915 | | |
| Pro | Ala | Ala | Asp | Glu | Ala | Gly | Gly | Thr | Ala | Gln | Val | Ile | Tyr | Ile | Asp |
| | | | 920 | | | | | 925 | | | | | 930 | | |
| Val | Gln | Ser | Met | Tyr | Gln | Pro | Gln | Ala | Lys | Pro | Glu | Glu | Lys | Lys | Lys |

```
                  935                    940                    945
Lys  Ser  Arg  Ser  Ser  Arg  Ser  Lys  Ile
              950                    955
```

( 2 ) INFORMATION FOR SEQ ID NO:7:

( i ) SEQUENCE CHARACTERISTICS:
        ( A ) LENGTH: 100 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:7:

```
GATCCGGTGG  AGGTGGTTCT  GGTGGAGGTG  GTTCAGGTGG  TGGAGGATCA  GGAGGTGGTG      60

GATCAGGTGG  AGGAGGTTCT  GGAGGTGGAG  GTTCCGGAAT                            100
```

( 2 ) INFORMATION FOR SEQ ID NO:8:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

```
GATATGTCGA  CGATGATGGA  TATTTACGTA  TGTTTG                                 36
```

( 2 ) INFORMATION FOR SEQ ID NO:9:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

```
GCATGGATCC  ACCTCCTCCA  GAATTTTCCT  TTGTCACCAC  ATACATAC                   48
```

( 2 ) INFORMATION FOR SEQ ID NO:10:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

```
CGCGTCCGGA  GGAGGTGGAT  CTGAACTTCT  AGATCCATGT  GGTTATATC                  49
```

( 2 ) INFORMATION FOR SEQ ID NO:11:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

```
GCATGCGGCC  GCCTATTCAA  TTTCTCCTTG  AGCAAAC                                37
```

( 2 ) INFORMATION FOR SEQ ID NO:12:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

GATATGTCGA CAAGATGTTG ACGTTGCAGA CTTGG         35

( 2 ) INFORMATION FOR SEQ ID NO:13:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

GCATGGATCC ACCTCCTCCT TCAATTTCTC CTTGAGCAAA C         41

( 2 ) INFORMATION FOR SEQ ID NO:14:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

CGCGTCCGGA GGAGGTGGTA GCCAGAAAAA GGGGGCTCCT CATG         44

( 2 ) INFORMATION FOR SEQ ID NO:15:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

GCATGCGGCC GCTAAGAATT TTCCTTTGTC ACCACATACA TAC         43

( 2 ) INFORMATION FOR SEQ ID NO:16:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

GCATAGATCT GGGCTCAGAA TTTTCCTTTG TCACCACATA CATAC         45

( 2 ) INFORMATION FOR SEQ ID NO:17:

( i ) SEQUENCE CHARACTERISTICS:
        ( A ) LENGTH: 38 base pairs
        ( B ) TYPE: nucleic acid
        ( C ) STRANDEDNESS: single ( D ) TOPOLOGY: linear ( i i ) MOLECULE TYPE: cDNA ( x i ) SEQUENCE DESCRIPTION: SEQ ID NO:17:

```
GCATAGATCT GGGCTCTTCA ATTTCTCCTT GAGCAAAC                    3 8
```